US012067699B2

(12) United States Patent
Takahashi et al.

(10) Patent No.: US 12,067,699 B2
(45) Date of Patent: Aug. 20, 2024

(54) PRODUCTION METHOD OF LEARNED MODEL, BRIGHTNESS ADJUSTMENT METHOD, AND IMAGE PROCESSING APPARATUS

(71) Applicant: Shimadzu Corporation, Kyoto (JP)

(72) Inventors: Wataru Takahashi, Kyoto (JP); Yusuke Tagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 588 days.

(21) Appl. No.: 17/282,229

(22) PCT Filed: Oct. 3, 2018

(86) PCT No.: PCT/JP2018/037075
§ 371 (c)(1),
(2) Date: May 19, 2021

(87) PCT Pub. No.: WO2020/070834
PCT Pub. Date: Apr. 9, 2020

(65) Prior Publication Data
US 2021/0350513 A1 Nov. 11, 2021

(51) Int. Cl.
G06T 5/00 (2024.01)
A61B 6/00 (2006.01)
(Continued)

(52) U.S. Cl.
CPC .............. G06T 5/92 (2024.01); A61B 6/5258 (2013.01); G06N 20/00 (2019.01); G06T 5/50 (2013.01)

(58) Field of Classification Search
CPC . G06T 2207/20081; G06T 2207/20084; G06T 5/001; G06T 5/007; G06T 7/0012; G06V 10/82
See application file for complete search history.

(56) References Cited

U.S. PATENT DOCUMENTS

2011/0305381 A1    12/2011  Ohno
2012/0288179 A1    11/2012  Ohno
(Continued)

FOREIGN PATENT DOCUMENTS

JP    WO2011/080808 A1    7/2011
JP    2011-255033 A       12/2011
JP    2015-181543 A       10/2015

OTHER PUBLICATIONS

Lore, Kin Gwn, Adedotun Akintayo, and Soumik Sarkar. "LLNet: A deep autoencoder approach to natural low-light image enhancement." Pattern Recognition 61 (2017): 650-662.*
(Continued)

Primary Examiner — Li Liu
(74) Attorney, Agent, or Firm — Muir Patent Law, PLLC

(57) ABSTRACT

This production method of a trained model (10) includes a step of optimizing a training model (11) so that a value of a loss function (A) becomes small. The loss function (A) is configured to output a relatively large value in a case where the contrast of the predetermined area (PA) in a brightness-adjusted image adjusted in brightness becomes high with respect to training data (20) than in a case where the contrast of the predetermined area in the brightness-adjusted image (3) becomes low with respect to the training data.

12 Claims, 11 Drawing Sheets

(51) Int. Cl.
      *G06N 20/00*      (2019.01)
      *G06T 5/50*      (2006.01)
      *G06T 5/92*      (2024.01)

(56) References Cited

U.S. PATENT DOCUMENTS

2015/0269749 A1   9/2015  Ohno
2021/0027436 A1*  1/2021  Banerjee .............. A61B 5/7267
2021/0150672 A1*  5/2021  Xu ........................... G06N 3/08

OTHER PUBLICATIONS

Written Opinion by the International Search Authority for PCT application No. PCT/JP2018/037075, dated Dec. 12, 2018, submitted with a machine translation.

\* cited by examiner (Second Embodiment)

(A) Change of the loss function (B) Predicted distribution of the brightness adjustment parameter

PRODUCTION METHOD OF LEARNED MODEL, BRIGHTNESS ADJUSTMENT METHOD, AND IMAGE PROCESSING APPARATUS

TECHNICAL FIELD

The present invention relates to a brightness adjustment method of a radiographic image.

BACKGROUND ART

Conventionally, it is known to perform a brightness adjustment on a medical radiographic image reflecting a subject so as to have brightness and contrast suitable for a diagnosis. Such a brightness adjustment of a radiographic image is disclosed in, for example, Japanese Unexamined Patent Application Publication No. 2015-181543.

In Japanese Unexamined Patent Application Publication No. 2015-181543, it is disclosed to perform a brightness adjustment of an input image by extracting a main subject area from an input image reflecting a subject, acquiring a representative value representing the brightness value in the area, calculating a gradation conversion coefficient for emphasizing or suppressing the contrast close to the representative value, and converting the brightness value (pixel value) of each pixel of the input image in accordance with a predetermined algorithm by using the calculated gradation conversion coefficient.

PRIOR ART DOCUMENT

Patent Document

Patent Document 1: Japanese Unexamined Patent Application Publication No. 2015-181543

SUMMARY OF THE INVENTION

Problems to be Solved by the Invention

In the brightness adjustment of the radiographic image, it is desirable to improve the visibility by enhancing the contrast in the area related to a diagnosis of a subject or the like in the image while preventing the occurrence of saturation of pixel values in the area. Saturation of a pixel value means that the information of the pixel is lost by the signal of the level exceeding the upper or lower limit of the pixel value. A pixel exceeding the upper limit is called "halation", and a pixel falling below the lower limit is called "black defects". As the contrast is increased by the brightness adjustment, the saturation of the pixel value more likely occurs. Therefore, it is preferable that the contrast of the pixel value in the area related to a diagnosis is increased as large as possible under the condition that no saturation occurs in the area related to the diagnosis of the subject.

In the technique disclosed in Japanese Unexamined Patent Application Publication No. 2015-181543, since the brightness adjustment is performed according to a certain algorithm, it is difficult to cope with exceptional cases, such as, e.g., the occurrence of the extraction error of the area and an artificial joint in which the pixel value distribution differs greatly from a usual distribution. Thus, halation or black defects may occur in the area related to the diagnosis of a subject or the like. For this reason, in recent years, an attempt has been made to directly output a brightness adjustment parameter from an input image using a trained model by machine learning. If the machine learning functions effectively, it is expected that the contrast can be increased as much as possible while suppressing the occurrence of halation and black defects in an area related to a diagnosis of a subject or the like, and that it is possible to deal with exceptional cases, such as, e.g., an artificial joint.

However, in machine learning, statistical learning is performed using a large amount of training data. Therefore, the brightness adjustment parameter to be output varies in a direction of increasing the contrast and in a direction of decreasing the contrast with respect to the optimal value (the value of increasing the contrast as much as possible under the condition that no saturation of a pixel value occurs in the area related to a diagnosis of a subject or the like). Therefore, in the trained model machine-trained such that the optimal value is output, when the brightness adjustment parameter to be output varies in the direction of increasing the contrast with respect to the optimal value, there is a problem that halation or black defects (saturation of a pixel value) may occur.

The present invention has been made to solve the above-mentioned problems. An object of the present invention is to provide a production method of a trained model, a brightness adjustment method, and an image processing apparatus capable of suppressing the occurrence of halation or black defects in an area related to a diagnosis of a subject or the like, in a brightness adjustment using a trained model by machine learning.

Means for Solving the Problem

In order to attain the above-described object, the production method of a trained model according to a first aspect of the present invention, a production method of a trained model by machine learning in which a radiographic image reflecting a subject is input and a brightness adjustment parameter of the radiographic image is output, the production method includes:

a step of outputting the brightness adjustment parameter of an input image by a training model with the input image as an input, the input image being included in training data;

a step of acquiring a value of a loss function related to the brightness adjustment parameter using the brightness adjustment parameter by the training model; and a step of optimizing the training model so that the value of the loss function becomes small, wherein in a case where contrast of a predetermined area in a brightness-adjusted image adjusted in brightness based on the brightness adjustment parameter becomes high with respect to the training data than in a case where the contrast of the predetermined area in the brightness-adjusted image becomes low with respect to the training data, the loss function is configured to output a relatively large value to bias the machine learning in a direction of decreasing the contrast.

In the trained model production method according to the first aspect of the present invention, by the above-described configuration, in a case where the contrast of the predetermined area in the brightness-adjusted image becomes high with respect to the training data, the loss function outputs a relatively large value. Therefore, it is possible to acquire a trained model in which it is suppressed that the brightness adjustment parameter is output to become a large contrast beyond the optimal value. That is, in the produced trained model, it is possible to bias the predictive distribution of the brightness adjustment parameter to be output to the radiographic image in the direction of decreasing the contrast with respect to the optimal value (the value that increases the contrast as much as possible under the condition that no saturation of the pixel value occurs in the predetermined area related to a diagnosis of a subject or the like). Thus, it is possible to suppress the occurrence of halation or black defects (saturation of a pixel value) in the predetermined area in the brightness-adjusted image by excessively increasing the contrast in the predetermined area. Thus, in the brightness adjustment using the trained model by the machine learning, it is possible to suppress the occurrence of halation or black defects in the area (predetermined area) related to a diagnosis of a subject or the like in the image.

In the production method of a trained model according to the first aspect of the present invention, in a case where halation or black defects occur due to saturation of a pixel value in the predetermined area in the brightness-adjusted image, the loss function is configured to output a relatively large value than in a case where saturation of a pixel value does not occur in the predetermined area. With this configuration, in a case where halation or black defects occur in the predetermined area, it is biased so that the value of the loss function becomes large. Therefore, it is possible to acquire a trained model trained so that the occurrence of halation or black defects in the predetermined area is suppressed.

In the production method of a trained model according to the first aspect of the present invention, in a case where the contrast of the brightness-adjusted image becomes high with respect to the training data than in a case where the contrast of the brightness-adjusted image becomes low with respect to the training data, the loss function includes a largely weighted weighting function. With this configuration, there is no need to prepare a plurality of loss functions to bias the output value according to the contrast, and therefore the value of the loss function can be easily biased by the weighting function.

In the production method of a trained model according to the first aspect of the present invention, the loss function is a function based on an error between a training parameter included in the training data and the brightness adjustment parameter with respect to the input image included in the training data. In the machine learning using a loss function based on an error of a brightness adjustment parameter, it is considered that errors vary symmetrically in the direction of decreasing the contrast and the direction of increasing the contrast with respect to the optimal value. Therefore, when learning is performed by an unbiased loss function, there is a possibility that the half of the predictive distribution of the brightness adjustment parameter to be output from the trained model varies in the direction of increasing the contrast with respect to the optimal value, causing halation or black defects (saturation of a pixel value). According to the above-described configuration, even by a loss function based on the error between the training parameter and the brightness adjustment parameter, it is possible to suppress that the error is evaluated symmetrically with respect to the optimal value. Thus, when the contrast becomes high with respect to the optimal value, it is possible to increase the value of the loss function relatively. As a result, it is possible to effectively suppress the occurrence of saturation of a pixel value in the predetermined area.

In the production method of a trained model according to the first aspect of the present invention, the loss function is a function based on a comparison between a pixel value a training image included in the training data and a pixel value of the brightness-adjusted image in which the input image included in the training data has been adjusted in the brightness based on the brightness adjustment parameter. Here, the training image is a brightness-adjusted image adjusted in the brightness based on the brightness adjustment parameter considered to be the optimal value. In the machine learning using a lost function based on a comparison of pixel values, when there is halation or black defects (saturation of a pixel value) in the brightness-adjusted image, it is underestimated by the amount of saturation of the pixel value in the area, which is likely to be biasedly trained in the direction of increasing the contrast. Consequently, in the trained model trained by an unbiased loss function, there is a possibility that the output brightness adjustment parameter varies in the direction of increasing the contrast with respect to the optimal value, and therefore halation or black defects (saturation of a pixel value) occurs. Therefore, according to the above-described configuration, even by the loss function based on the comparison of pixel values, it is possible to relatively increase the value of the loss function when the contrast becomes high with respect to the optimal value and suppress the underestimation of errors due to the saturation of the pixel value. Therefore, it is possible to effectively suppress the occurrence of saturation of the pixel value in the predetermined area.

In a case where the loss function is a function based on a comparison between the pixel value of the training image and the pixel value of the brightness-adjusted image, in a case where saturation of a pixel value occurs in the predetermined area in the image, the loss function is configured to output a value larger than in a case where saturation of a pixel value occurs in an area other than the predetermined area. Here, for example, the diagnosis importance level differs between the predetermined area reflecting a subject and the area of the background other than the predetermined area in the image. Therefore, in a case where saturation of a pixel value occurs in the predetermined area, by relatively increasing the value of the loss function and relatively decreasing the value of the loss function in the area other than the predetermined area, it is possible to suppress that the learning is affected by the error in the area other than the predetermined area while suppressing the occurrence of saturation of the pixel value in the predetermined area.

In this case, the loss function is set in magnitude of bias for each position in the input image, based on position information of the predetermined area included in the training data and bias information of the loss function. With this configuration, it is possible to distinguish between the predetermined area and the area other than the predetermined area based on the position information of the predetermined area and also possible to specify the magnitude relation of the bias of the loss function between the predetermined area and the area other than the predetermined area, based on the bias information of the loss function. Therefore, it is possible to easily differentiate the magnitude of the bias of the loss function according to the area in the image.

In the production method of a trained model according to the first aspect of the present invention, the predetermined area includes at least a part of the area reflecting the subject. With this configuration, in the image, a trained model in which the learning is biased in the direction of decreasing the contrast in the area reflecting a subject related to a diagnosis in the image. Therefore, it is possible to more assuredly suppress the occurrence of halation or black defects in the area reflecting a subject using the brightness adjustment parameter output by the trained model.

In the production method of a trained model according to the first aspect of the present invention, the brightness adjustment parameter includes a window level that defines a median of a pixel value range to be converted to the brightness-adjusted image in the radiographic image and a window width that defines magnitude of the pixel value range. In such a brightness adjustment by a window level and a window width, the magnitude of the contrast of the pixel value in the predetermined area can be adjusted. Therefore, the contrast can be easily evaluated by the loss function, as compared with a case where a large number of parameters affect the contrast.

A brightness adjustment method according to a second aspect of the present invention is a brightness adjustment method using machine learning in which a radiographic image reflecting a subject is input as an input and a brightness adjustment parameter of the radiographic image is output. The brightness adjustment method includes:

a step of acquiring the radiographic image;

a step of acquiring the brightness adjustment parameter with respect to the radiographic image using a trained model by the machine learning; and a step of acquiring a brightness-adjusted image by adjusting brightness of the radiographic image based on the brightness adjustment parameter, wherein the trained model is generated by learning that optimizes a loss function related to the brightness adjustment parameter, and wherein in a case where the contrast of a predetermined area in the brightness-adjusted image becomes high with respect to the training data of the machine learning than in a case where the contrast of the predetermined area in the brightness-adjusted image becomes low with respect to the training data, the loss function is configured to output a relatively large value to bias the machine learning in a direction of decreasing the contrast.

In the brightness adjustment method according to the second aspect of the present invention, with the above-described configuration, in a case where the contrast of the predetermined area in the brightness-adjusted image becomes high with respect to the training data, a value in which the loss function is relatively large is output. Consequently, in the trained model machine-trained by the loss function, the predictive distribution of the brightness adjustment parameter to be output to the radiographic image can be biased in the direction of decreasing the contrast with respect to the optimal value. Therefore, even by the trained model learned to output the optimal value, it is suppressed to output the brightness adjustment parameter to become high contrast exceeding the optimal value. Therefore, even if the brightness adjustment is performed using the output brightness adjustment parameter, it is possible to suppress the occurrence of halation or black defects (saturation of a pixel value) of the predetermined area in the brightness-adjusted image by excessively increasing the contrast of the predetermined area. Thus, in the brightness adjustment using a trained model by machine learning, it is possible to suppress the occurrence of halation or black defects in the area (predetermined area) related to a diagnosis of a subject or the like in the image.

In the brightness adjustment method according to the second aspect, the brightness adjustment method as recited in claim 10, further includes:

a step of acquiring information related to an imaging site or an imaging purpose of the subject, wherein in the step of acquiring the brightness adjustment parameter, the trained model for use in the brightness adjustment from a plurality of the trained models is selected based on the information related to the imaging site or the imaging purpose Note that the term "imaging site" denotes an individual site to be imaged, such as, e.g., a head, an abdomen, a lumbar region, and limbs of a subject. The imaging purpose denotes a diagnosis content desired to be grasped based on the captured image or an application of the image. For example, even in the case of a chest image, which lesion is to be grasped between the heart, the lungs, and the bones. Here, in a medical radiographic image, since the target to be depicted differs depending on the imaging site and the imaging purpose, there is a possibility that the optimal value of the brightness adjustment parameter may differ greatly. Therefore, by preparing a plurality of trained models separately trained according to the imaging site or the imaging purpose and selecting the trained model based on the imaging site or the imaging purpose, it is possible to perform the optimal brightness adjustment according to the imaging site or the imaging purpose.

An image processing apparatus according to a third aspect of the present invention, includes:

an image acquisition unit configured to acquire a radiographic image;

a storage unit configured to store a trained model by machine learning in which a radiographic image reflecting a subject is input and a brightness adjustment parameter of the radiographic image is output;

a parameter acquisition unit configured to acquire the brightness adjustment parameter with respect to the radiographic image using the trained model; and an adjustment processing unit configured to acquire a brightness-adjusted image by adjusting brightness of the radiographic image based on the brightness adjustment parameter, and wherein in a case where contrast of a predetermined area in the brightness-adjusted image adjusted in brightness becomes high with respect to training data of the machine learning than in a case where the contrast of the predetermined area in the brightness-adjusted image becomes low with respect to the training data, the loss function is configured to output a relatively large value to bias the machine learning in a direction of decreasing the contrast of the predetermined area in the brightness-adjusted image.

In the image processing apparatus according to the third aspect, with the above-described configuration, in the same manner as in the brightness adjustment method according to the second aspect, in the brightness adjustment using the trained model by the machine learning, it is possible to suppress the occurrence of halation or black defects in the area (predetermined area) related to a diagnosis of a subject or the like in the image.

Effects of the Invention

According to the present invention, as described above, it is possible to suppress the occurrence of halation or black defects in an area related to a diagnosis of a subject or the like in an image, in a brightness adjustment using a trained model by machine learning.

EMBODIMENTS FOR CARRYING OUT THE INVENTION

Hereinafter, embodiments in which the present invention is embodied will be described with reference to the attached drawings.

Referring to FIG. 1 to FIG. 15, a production method of a trained model, a brightness adjustment method, and an image processing apparatus according to a first embodiment will be described.

(Outline of Production Method of Trained Model, Brightness Adjustment Method, and Image Processing Apparatus)

Figure 1:
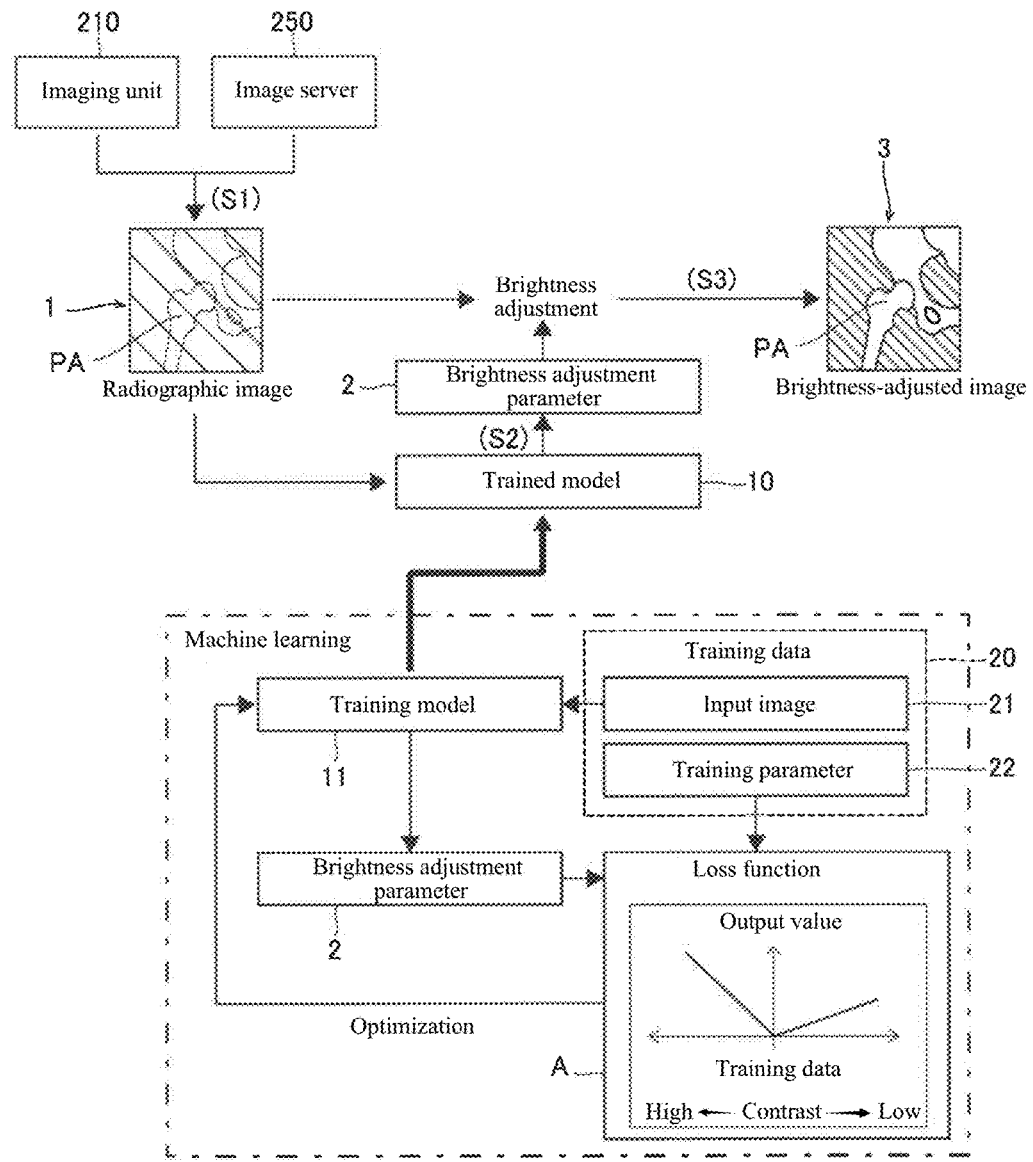
FIG. 1 is a diagram for explaining a brightness adjustment method and a production method of a trained model according to a first embodiment.

The brightness adjustment method according to the first embodiment shown in FIG. 1 is a brightness adjustment method using machine learning in which a captured radiographic image 1 reflecting a subject is input and a brightness adjustment parameter 2 of the radiographic image 1 is output.

Figure 2:
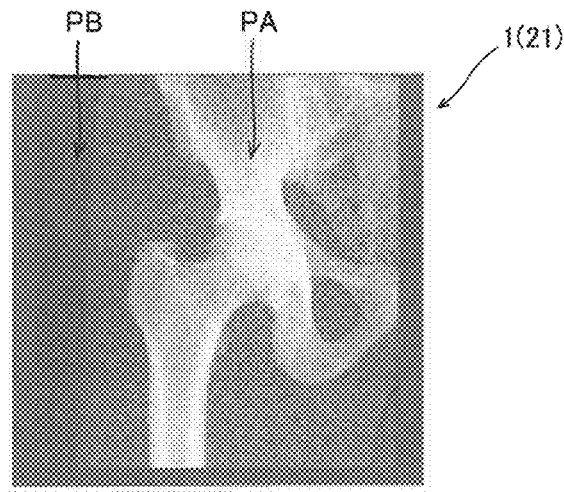
FIG. 2 is a diagram showing an example of a radiographic image.

The radiographic image 1 is a medical image used for, e.g., diagnose of a patient by a doctor or the like, and is, for example, an X-ray image as shown in FIG. 2. Specifically, the radiographic image 1 is a still image acquired by imaging a diagnosis region (lesion) of a subject by so-called simple roentgenography. The radiographic image 1 is a monochrome digital image in which the shading (light and dark) of each pixel is expressed by, for example, pixel values sectioned by a predetermined gradation number. FIG. 2 shows an example of a radiographic image 1 in which the periphery of the femur in the lumbar region of the subject is imaged. In the diagnosis by the radiographic image 1, the brightness adjustment of the radiographic image 1 is performed in order to more accurately grasp the state of the affected part which is the object of the diagnosis. The brightness adjustment is also referred to as a gradation conversion.

Specifically, as shown in FIG. 1, the brightness adjustment method of the first embodiment includes: Step S1 of acquiring a radiographic image 1; Step S2 of acquiring the brightness adjustment parameter 2 with respect to the radiographic image 1, using a trained model 10 by machine learning; and Step S3 for acquiring a brightness-adjusted image 3 by adjusting the brightness of the radiographic image 1, based on the brightness adjustment parameter 2.

In Step S1, for example, by the imaging unit 210 constituted by, e.g., an X-ray imaging device, a radiographic image 1 reflecting a subject is acquired. In Step S1, a radiographic image 1 previously stored in an image server 250 for storing images may be acquired from the image server 250.

In Step S2, when the radiographic image 1 to be subjected to a brightness adjustment is input, the trained model 10 outputs a brightness adjustment parameter 2 for the input image. The trained model 10 has been machine-trained to output the optimal brightness adjustment parameter 2 for the diagnosis with respect to the input image (radiographic image 1). The machine learning method is not particularly limited as long as it is suitable for the processing of outputting the brightness adjustment parameter 2 to the input image.

Figure 3:
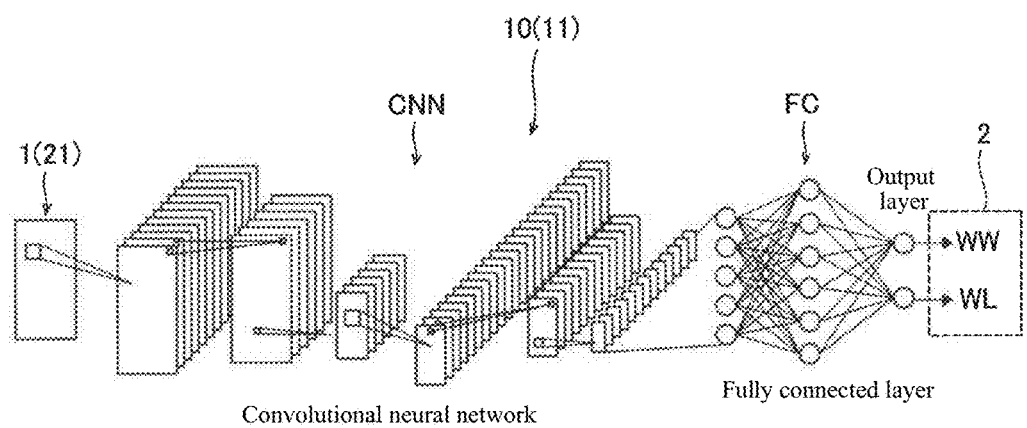
FIG. 3 is a diagram for explaining a trained model.

As one example, in the first embodiment, as shown in FIG. 3, the trained model 10 includes a front stage composed of a convolutional neural network CNN and a rear stage composed of a fully connected layer FC. Such a trained model 10 is considered to have a function of recognizing an image of a predetermined area which is crucial for the diagnosis from the radiographic image 1 by the convolutional neural network CNN of the front stage, and a function of converting the output of the front stage to a brightness adjustment parameter 2 by the fully connected layer FC of the rear stage. The trained model 10 is provided with a high-precision image recognition function of the convolutional neural network CNN. Therefore, it is expected to effectively suppress the saturation of a pixel value, such as, e.g., halation and black defects, in the area which is crucial for a diagnosis. It is also expected that the multi-layering (deepening) of the convolutional neural network CNN will be able to cope with exceptional cases, such as, e.g., individual differences of the individual radiographic image 1 and artificial joints.

As shown in FIG. 1, in order to generate the trained model 10 for performing the processing of outputting the brightness adjustment parameter 2, machine learning using a large amount of training data 20 is performed. In this specification, the state in the middle of learning by machine learning at the production stage of the trained model 10 is referred to as a training model 11. When the training model 11 has been machine-trained, it is referred to as a trained model 10.

In the first embodiment, the training data 20 used for machine learning includes an input image 21 and a training parameter 22. The input image 21 is a radiographic image (see FIG. 2) prepared in advance for learning and is an original image before the brightness adjustment is performed. The training parameter 22 is ground truth data generated as the optimal value of the brightness adjustment parameter output to the input image 21.

In a medical radiographic image, in order to improve the visibility of the region of interest, it is desirable to acquire the contrast as large as possible in the predetermined area PA (see FIG. 2) related to a diagnosis of a subject or the like in an image. On the other hand, in a medical radiographic image, it is desired that saturation of a pixel value, such as, e.g., so-called halation and black defects, does not occur in the predetermined area PA related to a diagnosis of a subject or the like in the image. On the other hand, in a medical radiographic image, for an area PB (see FIG. 2) other than the predetermined area PA of a subject in an image, such as, e.g., a background area and an area not related to the diagnosis, the decrease in the contrast or the occurrence of saturation in the pixel value is acceptable. Therefore, the optimal value of the brightness adjustment parameter in a medical radiographic image can be defined as a value that increases the contrast of the predetermined area PA as much as possible under the condition that saturation of a pixel value does not occur in the predetermined area PA related to a diagnosis. The training parameter 22 is an optimal value derived with respect to each input image 21 by, for example, the parameter adjustment operation by a training data generator.

When producing a trained model, an input image 21 is input and a brightness adjustment parameter 2 is output, and the learned model is made to learn the conversion processing from the input image 21 to the training parameter 22. In machine learning, a loss function for evaluating the difference between the output result (brightness adjustment parameter 2) of the training model 11 which is being trained and the training data (training parameter 22) is defined. The machine learning makes the inner parameter of the training model 11 optimize (train) to output an output result that minimizes the difference from the training data 20 by the optimization operation that reduces the loss function. The trained model 10 is produced by performing the optimization (learning) of the training model 11 over a sufficient number of times to converge the learning by using a sufficient amount of training data 20 to converge the learning. As described above, the trained model 10 is generated by performing the learning for optimizing a loss function related to the brightness adjustment parameter 2.

Here, in a case where the contrast of the predetermined area PA in the brightness-adjusted image 3 becomes high with respect to the training data 20 than in a case where the contrast of the predetermined area PA (see FIG. 2) in the brightness-adjusted image 3 becomes low with respect to the training data 20 of the machine learning, the loss function A of the first embodiment is configured to output a relatively large value to bias the learning in a direction of decreasing the contrast.

The predetermined area PA (see FIG. 2) is, as described above, an area related to a diagnosis of a subject or the like in the image in the medical radiographic image. The predetermined area PA includes at least a part of the area reflecting a subject. The predetermined area PA can be set to only a part of the area reflecting the subject, not the entire area reflecting the subject. The region of interest related to a diagnosis is a part of an area in which a disorder is considered to exist. Thus, the predetermined area PA may be a part of an area including the region of interest in the area reflecting the subject.

In Step S3, the processing of the brightness adjustment based on the brightness adjustment parameter 2 is performed. Consequently, a brightness-adjusted image 3 in which the brightness of the input radiographic image 1 has been adjusted is acquired. The brightness-adjusted image 3 is output to, e.g., a display device and is used for a diagnosis by a doctor or the like.

[Brightness Adjustment Parameter]

Next, the brightness adjustment parameter 2 output by the trained model 10 will be described. In the first embodiment, the content of the brightness adjustment (gradation conversion) processing is not particularly limited, and the brightness adjustment parameter 2 is not particularly limited as long as it corresponds to the brightness adjustment processing of an image. In the first embodiment, as one example, a brightness adjustment by windowing processing for converting a partial range of a gradation range of the input image into a gradation range for displaying will be described.

Figure 4:
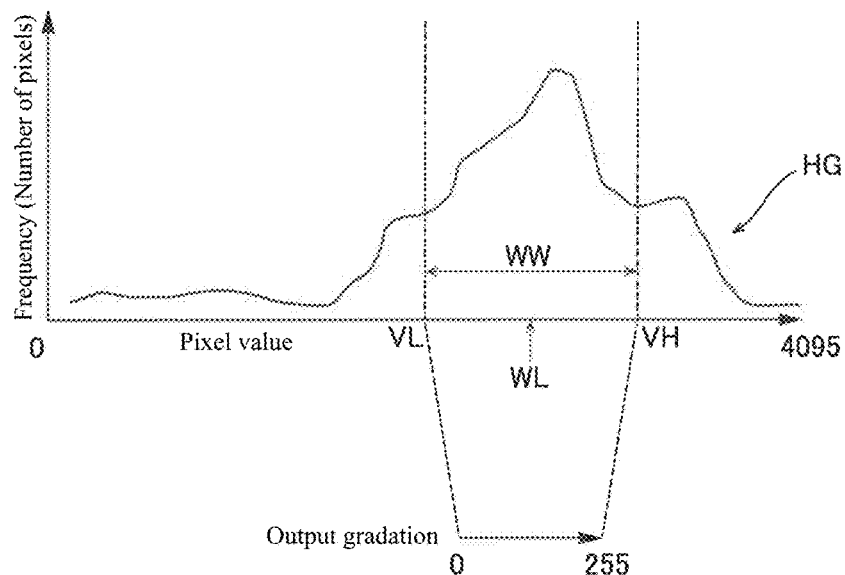
FIG. 4 is a diagram for explaining the content of a brightness adjustment.

FIG. 4 is a conceptual diagram of a histogram HG of pixel values (gradations) in the radiographic image 1 and an output gradation after the brightness adjustment. The horizontal axis of the histogram HG represents a pixel value of the input image, and the vertical axis of the histogram HG represents the number of pixels (frequency) having its pixel value.

In the window process, a part of the gradation range specified by the brightness adjustment parameter 2 in the input image is extracted and converted to match the output gradation range after the brightness adjustment. With this, in the window processing, the pixel value range of the image portion constituting the predetermined area PA (see FIG. 2) related to a diagnosis is specified by the brightness adjustment parameter 2, so that the contrast of the predetermined area PA can be adjusted. Further, in the window processing, it is possible to extract a part of the gradation range in the original radiographic image 1 and convert it to a gradation range that the display device can output. As shown in FIG. 4, the gradation number of the medical radiographic image is generally greater than the gradation number that the display device can display. For example, a medical radiographic image is image data having a pixel value of 4,096 gradations (12 bit) ranging from 0 to 4,095. On the other hand, a typical display device displays 256 gradations (8 bit) ranging from 0 to 255. Hereinafter, an example of the window processing for converting an input image of 4,096 gradations to a gradation range of 256 gradations will be described.

The brightness adjustment parameter 2 includes: a window level WL that defines the median of the pixel value range to be converted to the brightness-adjusted image 3 in the radiographic image 1; and a window width WW that defines the size of the pixel value range. In the brightness adjustment processing, a brightness adjustment is performed by assigning the gradation range of a window width WW centered on the window level WL to output gradations (0 to 255). At this time, in the radiographic image 1, a pixel having a pixel value (0 to VL) that is equal to or lower than the lower limit VL of the window width WW is converted to the lowest gradation (0 gradations) in the brightness-adjusted image 3. In the radiographic image 1, a pixel having a pixel value (VH to 4,095) which is equal to or higher than the upper limit VH of the window width WW is converted to the maximum gradation (255 gradations) in the brightness-adjusted image 3. With this, the brightness-adjusted image 3 becomes an image represented by the gradation number corresponding to the output gradation. The gradation range of the window width WW may be larger or smaller than the output gradation range (256 gradations).

Figure 5:
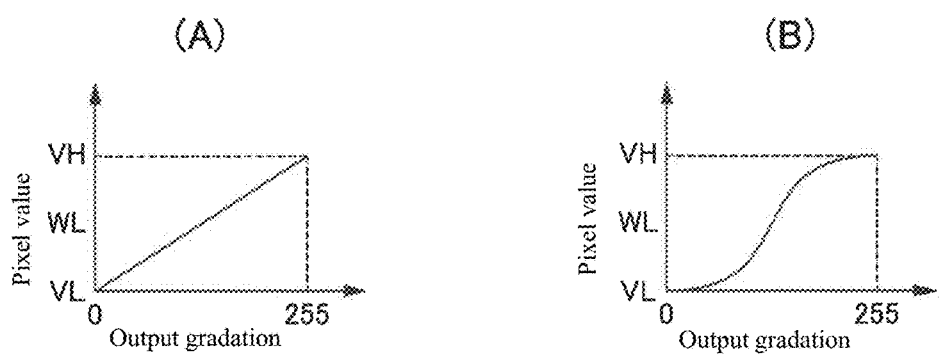
FIG. 5 is a diagram showing a first example (A) and a second example (B) of a gradation conversion.

FIG. 5 shows examples of conversion characteristics (density conversion curves) when the gradation range of the window width WW is converted to the output gradations (0 to 255). In the brightness adjustment, as shown in (A) of FIG. 5, the gradation range of the window width WW may be converted to the output gradation by a linear expression (linear transformation characteristic), or as shown in (B) of FIG. 5, the gradation range of the window width WW may be converted to the output gradation by a nonlinear transformation characteristic, such as, e.g., a quadratic and a logarithmic function. In the case as shown in (B) of FIG. 5, the brightness adjustment parameter 2 may include an additional parameter that determines the transformation characteristics (shape of the concentration conversion curve).

Figure 6:
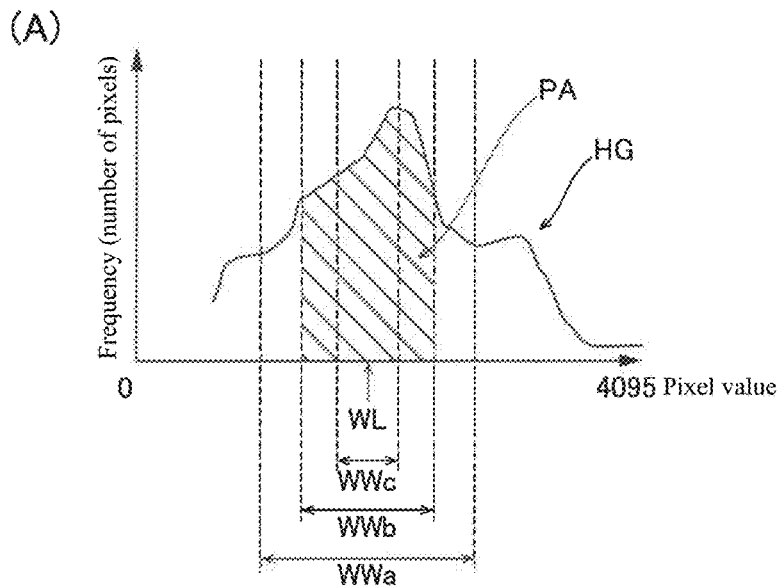
FIG. 6 is a diagram (A) showing a plurality of window widths and diagrams (B) to (D) for explaining gradation conversions in respective window widths.
Figure 6:
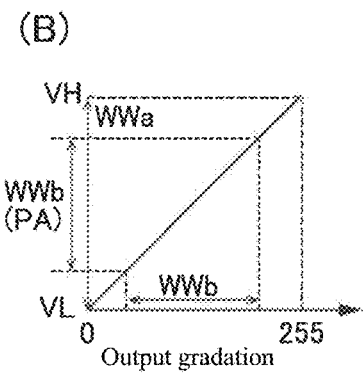
Figure 6:
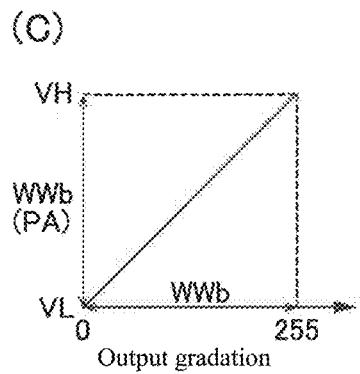
Figure 6:
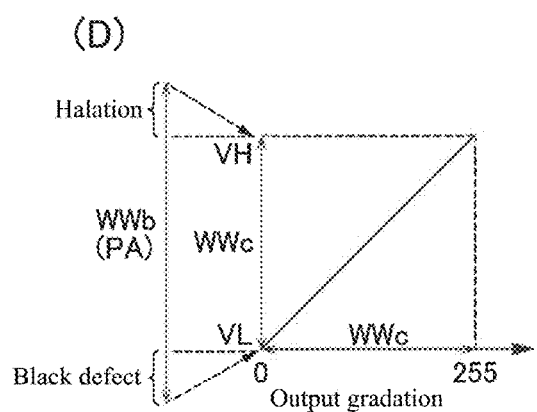

As shown in (A) of FIG. 6, it is assumed that the image portion of the predetermined area PA is composed of pixels included in, e.g., the hatched area of the histogram HG. At this time, it is assumed that the window width WW is set in three patterns: the WWa which is larger than the gradation range of the predetermined area PA; the WWb which coincides the gradation range of the predetermined area PA; and the WWc which is smaller than the gradation range of the predetermined area PA.

When the window width WW is set by WWa, as shown in (B) of FIG. 6, the gradation range WWb of the predetermined area PA is expressed by a part of the output gradation range (0 to 255) in the brightness-adjusted image 3. The predetermined area PA is expressed by a range narrower than 256 gradations.

When the window width WW is set by WWb, as shown in (C) of FIG. 6, the gradation range WWb of the predetermined area PA is expressed by the entire range of the output gradation range (0 to 255) in the brightness-adjusted image 3. Therefore, the contrast increases as compared with the case where the window width WW is set by WWa.

When the window width WW is set by WWc, as shown in (D) of FIG. 6, the gradation range WWb of the predetermined area PA becomes wider than the window width WWc, and therefore, among the pixels constituting the predetermined area PA, as for the pixels having pixel values outside the window width WWc (pixel values equal to or larger than the upper limit VH of the window width WWc and pixel values equal to or lower than the lower limit VL of the window width WWc), the pixel value is saturated in the brightness-adjusted image 3, and therefore it is expressed as 0 gradation or 255 gradations. As for the pixels belonging to the inside of the window width WWc in the predetermined area PA, it is expressed by the entire range of the output gradation range (0 to 255) in the brightness-adjusted image 3, and therefore the contrast increases.

Thus, in the brightness adjustment parameter 2, as the window width WW becomes smaller, the contrast of the predetermined area PA in the brightness-adjusted image 3 increases. In other words, as the window width WW is reduced, the shading (light and dark) of the pixels included in the predetermined area PA can be expressed with more gradation numbers in the brightness-adjusted image 3. Therefore, the contrast resolution increases. On the other hand, if the window width WW is set too small, the saturation of pixel values, such as, e.g., halation and black defects, occurs in the predetermined area PA of the brightness-adjusted image 3. The larger the window width WW, the smaller the contrast of the predetermined area PA in the brightness-adjusted image 3. As the window width WW is increased, the contrast of the predetermined area PA in the brightness-adjusted image 3 is decreased. As the window width WW increases, the shading (light and dark) of the pixels included in the predetermined area PA is expressed with the smaller number of gradations, and therefore the contrast resolution decrease.

(Loss Function)

Next, the loss function will be described. As shown in FIG. 1, the training data 20 (training parameter 22) used in machine learning is to provide the optimal value (ground truth) of the brightness adjustment parameter 2. Therefore, the gradation range WWb (see FIG. 6) is designed to be the window width WW as much as possible. The trained model 10 is configured to output the value of the window width WW corresponding to the gradation range Wb as the brightness adjustment parameter 2 with respect to the input radiographic image 1 by the optimization using the loss function. Therefore, in a case where the window width WW as the brightness adjustment parameter 2 varies in a direction in which the window width WW as the brightness adjustment parameter 2 is larger than the optimal value (WWb), the contrast becomes low as compared with the optimal value. Thus, the brightness adjustment is performed in the direction in which the saturation of the pixel value in the predetermined area PA is less likely to occur. On the other hand, in a case where the window width WW as the brightness adjustment parameter 2 varies in a direction in which the window width is smaller than the optimal value (WWb), as compared with the optimal value, the contrast becomes high. Thus, the brightness adjustment is performed in a direction in which the saturation of the pixel value, such as, e.g., halation and black defects, is likely to occur in the predetermined area PA.

Therefore, as shown in FIG. 1, in the first embodiment, in a case where the contrast of the predetermined area PA in the brightness-adjusted image 3 becomes high with respect to the training data 20 than in a case where the contrast of the predetermined area PA in the brightness-adjusted image 3 becomes low with respect to the training data 20 of the machine learning, the loss function A is configured to output a relatively large value to bias the learning in a direction of decreasing the contrast.

That is, the loss function A is a function designed such that in a case where the brightness adjustment parameter 2 output from the training model 11 which is being trained has an error in a direction of decreasing the contrast with respect to the training data 20 which is the optimal value, the error is evaluated relatively small, and in a case where the brightness adjustment parameter 2 output from the training model 11 which is being trained has an error in a direction of increasing the contrast with respect to the training data 20 which is the optimal value, the error is evaluated relatively large. In the machine learning, the training model 11 is optimized so that the loss function A is reduced. Therefore, the output value of the loss function A increases with respect to the error in the direction of increasing the contrast. As a result, the training model 11 is biased in a direction of suppressing the contrast.

Therefore, in a case where the brightness adjustment parameter 2 output from the training model 11 which is being trained outputs a window width WW smaller than the training parameter 22 which is the optimal value (WWb) and saturation of a pixel value (halation or black defects) occurs in the predetermined area PA, the loss function A is estimated relatively large. As described above, in the first embodiment, in a case where halation or black defects occur due to saturation of a pixel value in the predetermined area PA in the brightness-adjusted image 3, the loss function A is configured to output a value relatively larger than in a case where no saturation of a pixel value occurs in the predetermined area PA.

Specific examples of the loss function A are shown. In the first embodiment, the loss function A is a function based on the error of the training parameter 22 included in the training data 20 and the brightness adjustment parameter 2 with respect to the input image 21 included in the training data 20.

Further, in a case where the contrast of the brightness-adjusted image 3 becomes high with respect to the training data 20 than in a case where the contrast of the brightness-adjusted image 3 becomes low with respect to the training data 20, the loss function A includes a highly weighted weighting function.

For example, the loss function A is a weighted mean squared error shown in the following Expression (1).

$$A = \sqrt{(WL-WL_0)^2 + \{f(WW-WW_0)\}^2} \quad (1)$$

Here, $$f(r) = \begin{cases} wr, & r < 0 \\ r, & r \geq 0 \end{cases}$$

In the above Expression (1), WL and WW are a window level and a window width (brightness adjustment parameters 2), respectively, which are output by the training model 11 which is being trained to the input image 21. $WL_0$, $WW_0$ are a window level and a window width (training parameters 22) included in the training data 20. $WW_0$ is a value corresponding to the optimal value (WWb) illustrated in FIG. 6 f(r) is a weighting function. w is a value of the weight (w>1).

In the case where the error ($WW-WW_0$) between the output result of the training model 11 and the training data 20 becomes negative (in the case where the window width WW is smaller than the optimal value and the contrast is high), the weighting function f(r) estimates the error relatively large by adding the value of the weight w. In the case where the error ($WW-WW_0$) between the output result of the training model 11 and the training data 20 is positive (in the case where the window width WW is larger than the optimal value and the contrast is low), the weighting function f(r) outputs the error as it is without adding the weight w. The weight w is not particularly limited, but is, for example, 10. In this case, the loss function A evaluates the error 10 times larger when the error ($WW-WW_0$) becomes negative as compared with the case when the error ($WW-WW_0$) becomes positive.

As a result, in a case where the contrast of the predetermined area PA in the brightness-adjusted image 3 becomes high with respect to the training data 20 (when the error ($WW-WW_0$) becomes negative), the loss function A outputs a relatively large value to bias the learning in a direction of decreasing the contrast.

Figure 7:
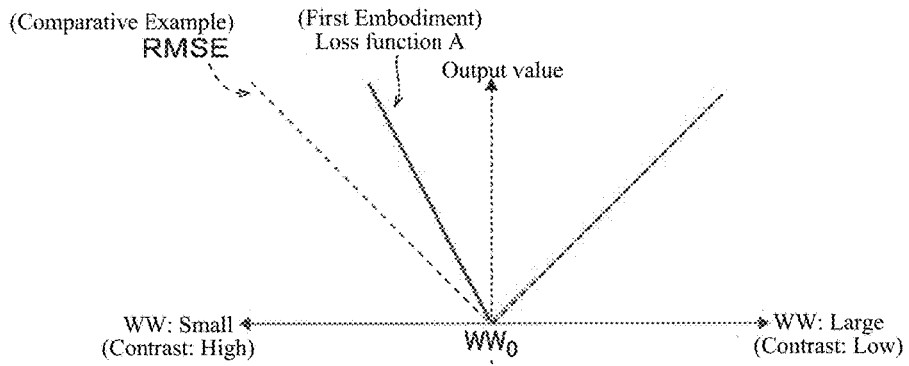
FIG. 7 is a diagram showing the change (A) in the loss-coefficient and the predictive distribution (B) of the brightness adjustment parameter according to the first embodiment.
Figure 7:
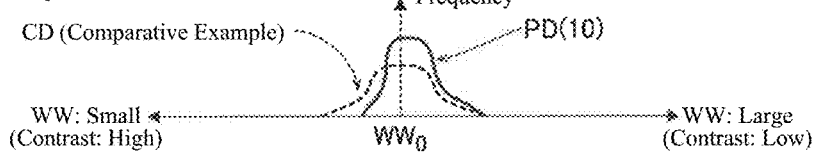

Next, referring to FIG. 7, the effect of the learning bias by the loss function A in the first embodiment on the brightness adjustment parameter 2 output by the trained model 10 will be described. (A) of FIG. 7 is a graph showing the change in the output value (vertical axis) of the loss function A with respect to the window width WW (horizontal axis). (B) of FIG. 7 is a graph showing the predictive distribution PD of the window width WW output by the trained model 10 optimized using the loss function A. The predictive distribution PD indicates the frequency (probability) that the trained model 10 outputs the value of each window width WW.

As Comparative Example, a case using a loss function RMSE by a simplified mean square error without weighting is shown in dashed lines. The loss function RMSE of Comparative Example is represented by the following Expression (2).

$$RMSE = \sqrt{(WL-WL_0)^2 + (WW-WW_0)^2} \quad (2)$$

As can be seen from the above Expression (2) and (A) of FIG. 7, the loss function RMSE according to Comparative Example is symmetrical with respect to the error direction (the magnitude of the window width WW). Therefore, it is considered that the predictive distribution CD of the output result of the trained model optimized using the loss function RMSE is symmetrically distributed with respect to the optimal value $WW_0$. As described above, in a case where the window width WW to be output is shifted to a smaller side with respect to the optimal value $WW_0$, it is considered that saturation of a pixel value occurs in the predetermined area PA. In the trained model optimized using the loss function RMSE according to Comparative Example, the saturation of a pixel value may occur in the predetermined area PAs in approximately half of the cases of the window width WW to be output due to the symmetry of the predictive distribution CD of the output result.

On the other hand, the loss function A shown by the solid line in FIG. 7 is asymmetrically biased because the window width WW is estimated to be larger by the weighting factor w in the direction smaller than the optimal value (training data 20) while taking the minimum value by the optimal value ($WW_0$).

For this reason, the predictive distribution PD of the output result of the trained model 10 optimized by using the loss function A of the first embodiment becomes a distribution biased in a direction of decreasing the contrast (a direction of increasing the window width WW) with respect to the optimal value $WW_0$ than in a direction of increasing the contrast (a direction of decreasing the window width WW).

As a result, as can be seen from the predictive distribution PD, in the trained model 10 optimized using the loss function A of the first embodiment, the window width WW to be output is suppressed from varying in the direction of increasing the contrast (the direction of decreasing the window width WW) beyond the optimal value $WW_0$, and the possibility of generating saturation of a pixel value in the predetermined area PA is suppressed.

(Image Processing Apparatus)

Next, referring to FIG. 8 and FIG. 9, the image processing apparatus 100 according to the first embodiment will be described. The image processing apparatus 100 is configured to perform brightness adjustment processing on a radiographic image 1 reflecting a subject using a trained model 10 by machine learning that outputs a brightness adjustment parameter 2 of a radiographic image 1. That is, the image processing apparatus 100 is configured as a device for performing the brightness adjustment method according to the first embodiment described above.

Figure 8:
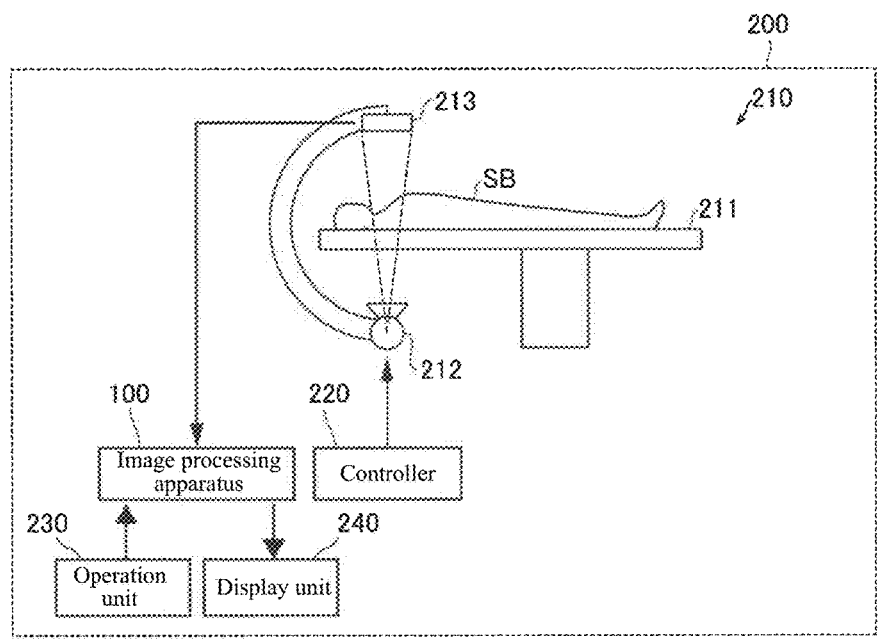
FIG. 8 is a diagram for explaining an imaging system equipped with an image processing apparatus according to the first embodiment.

In the example of FIG. 8, the image processing apparatus 100 is configured as a part of an imaging system 200 for capturing a radiographic image 1 of a subject. The imaging system 200 is provided with an imaging unit 210, a controller 220, an image processing apparatus 100, an operation unit 230, and a display unit 240. The operation unit 230 is an input device, such as, e.g., a keyboard and a mouse. The display unit 240 is constituted by an image display device, such as, e.g., a liquid crystal display device.

The imaging unit 210 includes a top board 211, an X-ray irradiation unit 212, and an X-ray detection unit 213. The top board 211 is configured to support a subject SB (human). The X-ray irradiation unit 212 is configured to emit X-rays toward the subject SB. The X-ray detection unit 213 is constituted by, for example, an FPD (Flat Panel Detector) and is configured to detect the X-rays emitted from the X-ray irradiation unit 212 and transmitted through the subject SB. By the imaging unit 210, the X-ray image (see FIG. 2) reflecting the region of interest of the subject is acquired as a radiographic image 1.

The controller 220 is a computer configured to control the imaging operation of the imaging unit 210. The controller 220 performs various controls, such as, e.g., the control of the moving mechanism (not shown) for moving the top board 211, the X-ray irradiation unit 212, and the X-ray detection unit 213, the control of the X-ray irradiation by the X-ray irradiation unit 212, and the setting of the imaging condition.

Further, the image processing apparatus 100 is connected to the imaging unit 210, the operation unit 230, and the display unit 240. The image processing apparatus 100 acquires the detection signal of X-rays from the X-ray detection unit 213 of the imaging unit 210 and acquires the radiographic image 1 based on the acquired detection signal. The image processing apparatus 100 performs the brightness adjustment of the radiographic image 1 (see FIG. 1) to acquire the brightness-adjusted image 3 (see FIG. 1).

Figure 9:
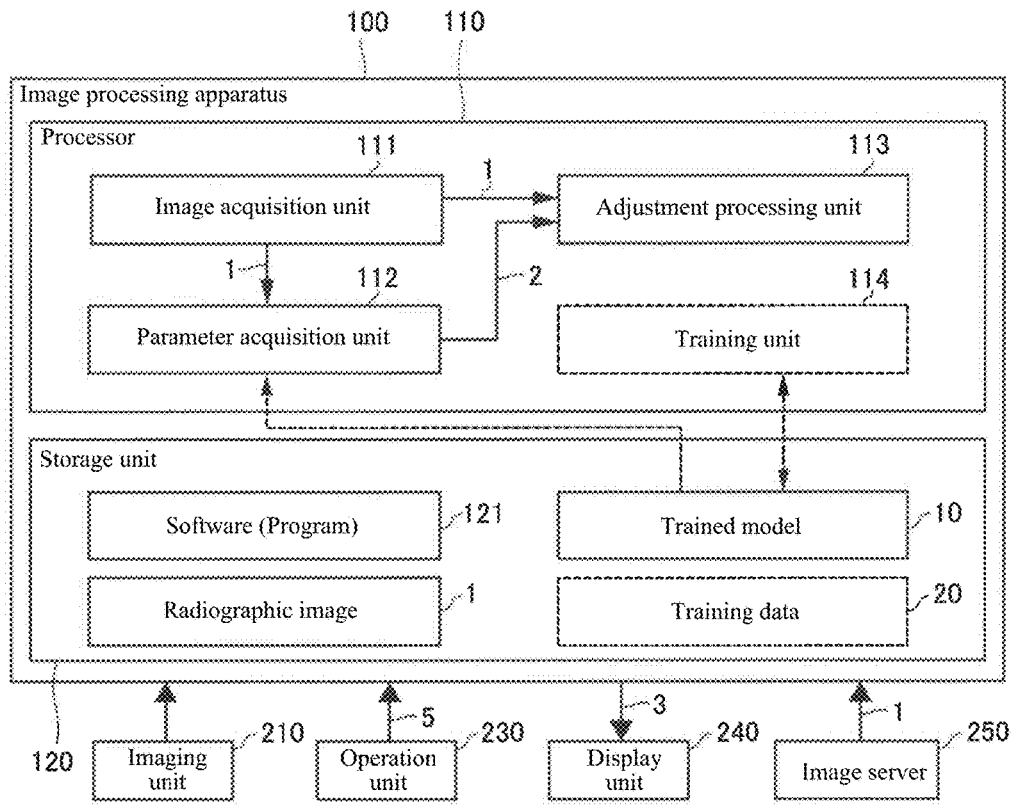
FIG. 9 is a block diagram for explaining the configuration of the image processing apparatus.

As illustrated in FIG. 9, the image processing apparatus 100 is configured by a computer including a processor 110, such as, e.g., a CPU (Central Processing Unit), a GPU (Graphics Processing Unit), a dedicated FPGA (field-programmable gate array), and a storage unit 120, such as, e.g., a ROM, a RAM, a volatile or a non-volatile storage device (HDD, SSD (solid state drive)). The image processing apparatus 100 may be configured by a computer (a personal computer, a workstation, a supercomputer, etc.) on which predetermined software (program) is installed in a storage unit, or a computer system consisting of a plurality of computers.

In the first embodiment, the image processing apparatus 100 is provided with an image acquisition unit 111, a parameter acquisition unit 112, and an adjustment processing unit 113. The image acquisition unit 111, the parameter acquisition unit 112, and the adjustment processing unit 113 are configured as, for example, functional blocks of the processor 110. That is, the processor 110 of the computer functions as the image acquisition unit 111, the parameter acquisition unit 112, and the adjustment processing unit 113 by executing the programs 121 stored in the storage unit 120.

The image acquisition unit 111 is configured to acquire the radiographic image 1. The image acquisition unit 111 generates the radiographic image 1, based on, for example, the detection signal acquired from the X-ray detection unit 213. The image acquisition unit 111 can acquire the radiographic image 1 by reading out the radiographic image 1 stored in the storage unit 120 from the storage unit 120 or by receiving the radiographic image 1 from an external image server 250 via a network. The image acquisition unit 111 outputs the acquired radiographic image 1 to the parameter acquisition unit 112 and the adjustment processing unit 113.

The parameter acquisition unit 112 is configured to acquire the brightness adjustment parameter 2 with respect to the radiographic image 1 using the trained model 10 stored in the storage unit 120. That is, the parameter acquisition unit 112 acquires the brightness adjustment parameter 2 including the window level WL and the window width WW by inputting the radiographic image 1 acquired from the image acquisition unit 111 to the trained model 10. The parameter acquisition unit 112 outputs the acquired brightness adjustment parameter 2 to the adjustment processing unit 113.

The adjustment processing unit 113 is configured to acquire the brightness-adjusted image 3 by adjusting the brightness of the radiographic image 1 based on the brightness adjustment parameter 2. The adjustment processing unit 113 performs the window processing based on the brightness adjustment parameter 2 (the window level WL, the window width WW) acquired from the parameter acquisition unit 112 to acquire the brightness-adjusted image 3. The adjustment processing unit 113 outputs the acquired brightness-adjusted image 3 to the display unit 240 and makes the storage unit 120 store it. Further, the adjustment processing unit 113 receives an input operation from the operator via the operation unit 230. The adjustment processing unit 113 can receive a direct input of the brightness adjustment parameter 2 by the operator through the operation unit 230. When the input of the brightness adjustment parameter 2 is received, the adjustment processing unit 113 performs the brightness adjustment based on the input brightness adjustment parameter 2.

The storage unit 120 stores the trained model 10 by machine learning in which the radiographic image 1 reflecting a subject is input and the brightness adjustment parameter 2 of the radiographic image 1 is output. That is, as shown in FIG. 1, the storage unit 120 stores the trained model 10 generated in advance by the learning for performing the optimization of the loss function A related to the brightness adjustment parameter 2.

The storage unit 120 also stores the program 121 to be executed by the processor 110 and the radiographic image 1. Further, the storage unit 120 stores the acquired brightness-adjusted image 3.

Instead of constructing the image acquisition unit 111, the parameter acquisition unit 112, and the adjustment processing unit 113 of the image processing apparatus 100 realized by executing software by a processor as functional blocks, hardware dedicated for performing the respective processing may be constructed.

(Brightness Adjustment Processing)

Figure 10:
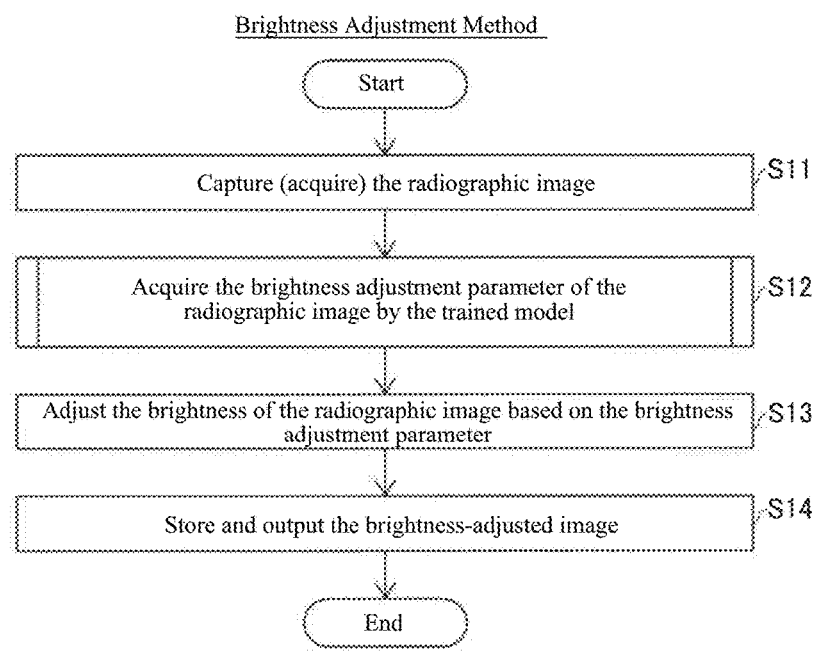
FIG. 10 is a flowchart for explaining a brightness adjustment method by the image processing apparatus.
Figure 11:
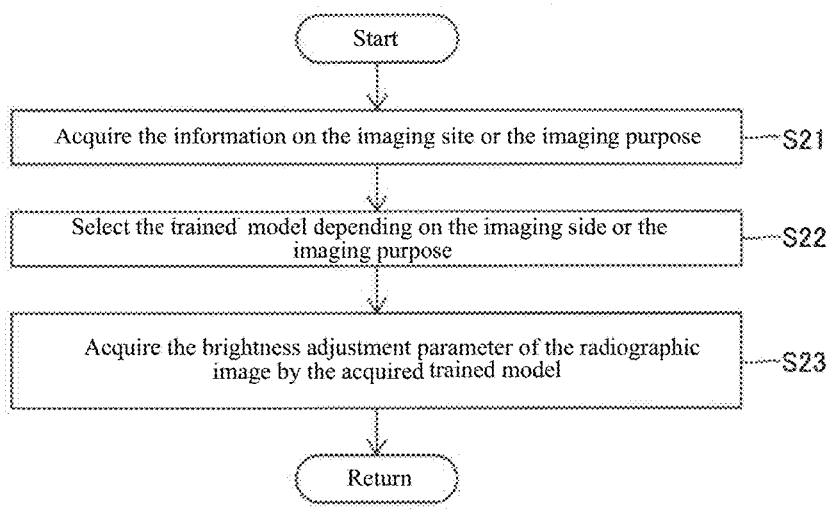
FIG. 11 is a flow diagram of acquisition processing (subroutine) of a brightness adjustment parameter.
Figure 12:
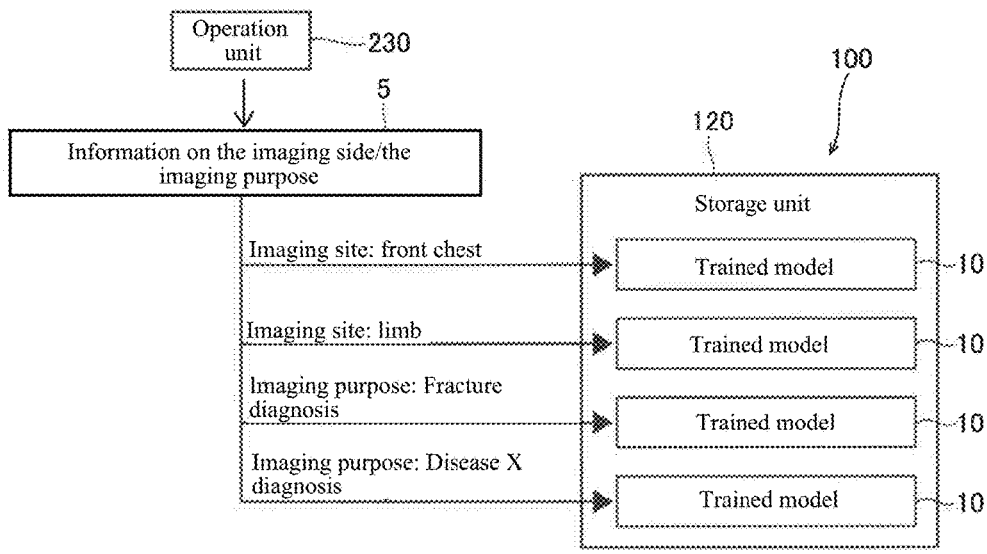
FIG. 12 is a diagram for explaining information related to an imaging site or an imaging purpose.

Referring to FIG. 10 to FIG. 12, the brightness adjustment processing according to the image processing apparatus 100 will be described. The brightness adjustment processing shown in FIG. 10 to FIG. 12 performs the brightness adjustment method of the first embodiment by the image processing apparatus 100.

In Step S11 of FIG. 10, for example, by performing imaging by the imaging unit 210, the image acquisition unit 111 acquires the radiographic image 1. In Step S12, the parameter acquisition unit 112 performs the processing of acquiring the brightness adjustment parameter 2 of the radiographic image 1 by the trained model 10 stored in the storage unit 120. In the first embodiment, the processing of acquiring the brightness adjustment parameter 2 includes Steps S21 to S23 in FIG. 11.

That is, the brightness adjustment method of the first embodiment includes Step S21 for acquiring the information 5 related to the imaging site or the imaging purpose of the subject, as shown in FIG. 11.

Specifically, as shown in FIG. 12, the parameter acquisition unit 112 receives the information input via the operation unit 230 to acquire the information 5 related to the imaging site or the imaging purpose of the subject.

The information of the imaging site is information indicating which part is imaged, such as, e.g., the front chest, the side, the front abdomen (lumbar part), the front, limb bones (e.g., the front of the knee joint, the side, the hand part), and the like. The information on the imaging purpose is information about the diagnosis of fractures, the diagnosis of a certain disease, or the like. For example, the optimal value of the brightness adjustment parameter 2 differs between the case of examining the condition of the pulmonary and the cardiac tissue (e.g., presence or absence of tumors, bronchial and vascularization) in the radiographic image of the front chest and examining the condition of the femur and other bone conditions (e.g., fractures, dislocations, bone deformities) in the radiographic image 1 in the lumbar region as shown in FIG. 2.

Therefore, in the first embodiment, the storage unit 120 is storing in advance a plurality of trained models 10 corresponding to the information 5 about the imaging site or the imaging purpose. Each trained model 10 has been trained to output the optimal brightness adjustment parameter 2 with respect to the radiographic image 1 corresponding to the imaging site and the imaging purpose. For example, in the trained model 10 for the front chest, the brightness adjustment parameter 2 for the image of the front chest is trained by using the training data 20 for performing the optimal brightness adjustment for confirming the state of the pulmonary tissue and the cardiac tissue. The storage unit 120 stores the respective trained models 10 in association with the information 5 related to the imaging site or the imaging purpose.

Then, in Step S22 of FIG. 11, the parameter acquisition unit 112 selects the trained model 10 used for the brightness adjustment from the plurality of trained models 10, based on the information 5 related to the imaging site or the imaging purpose. As a result, the parameter acquisition unit 112 acquires the trained model 10 according to the imaging site or the imaging purpose.

In Step S23, the parameter acquisition unit 112 acquires the brightness adjustment parameter 2 of the radiographic image 1 according to the selected trained model 10. Thus, in the brightness adjustment method of the first embodiment, in the step of acquiring the brightness adjustment parameter 2, based on the information 5 related to the imaging site or the imaging purpose, the trained model 10 used for the brightness adjustment is selected from the plurality of trained models 10. The brightness adjustment parameter 2 of the radiographic image 1 is acquired by the selected trained model 10.

Returning to FIG. 10, in Step S13, the adjustment processing unit 113 performs the brightness adjustment of the radiographic image 1 based on the acquired brightness adjustment parameter 2. Thus, the adjustment processing unit 113 acquires the brightness-adjusted image 3. In Step S14, the adjustment processing unit 113 makes the acquired brightness-adjusted image 3 store in the storage unit 120 and outputs it to the display unit 240.

As described above, the brightness adjustment method of the first embodiment according to the image processing apparatus 100 is performed.

(Production Method of Trained Model)

Next, referring to FIG. 13 to FIG. 15, the production method of the trained model according to the first embodiment will be described.

Figure 13:
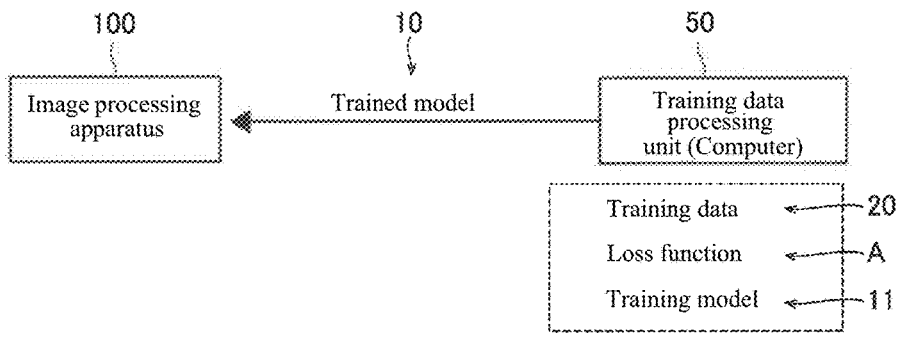
FIG. 13 is a diagram showing trained-data processing unit for performing machine learning.

As shown in FIG. 13, the production (machine learning) of the trained model 10 can be performed by a training data processing unit 50 provided separately from the image processing apparatus 100. The training data processing unit 50 is configured by a computer (e.g., a personal computer, a workstation, or a supercomputer) in which a predetermined software (program) is installed in a storage unit or a computer system comprising a plurality of computers.

The production method of the trained model 10 is a method of producing a trained model by machine learning in which a radiographic image 1 reflecting a subject is input and the brightness adjustment parameter 2 of the radiographic image 1 is output. The training data processing unit 50 stores the training data 20 including the input image 21 and the training parameter 22, the loss function A, and the training model 11 for learning in a storage unit and produces the trained model 10 by machine learning. The training data processing unit 50 stores a leaning data set of a plurality of training data 20 required for converging the machine learning.

Figure 14:
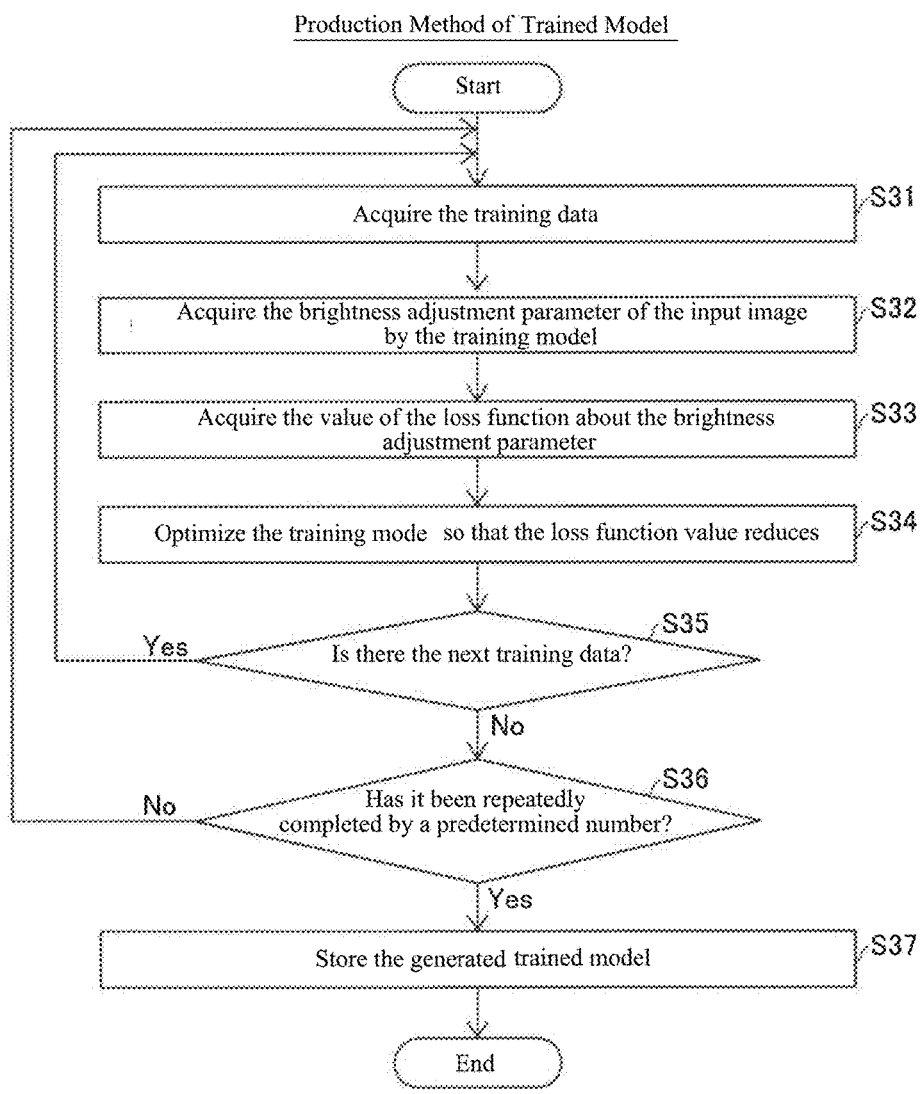
FIG. 14 is a flowchart for explaining a production method of a trained model according to the first embodiment.
Figure 15:
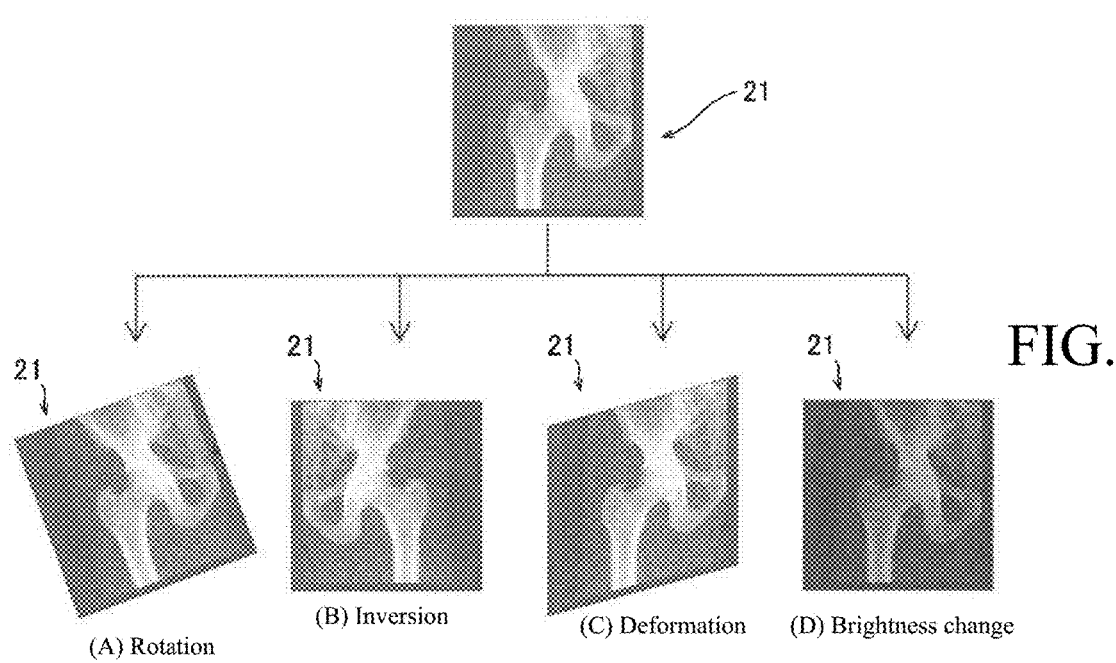
FIG. 15 is a diagram for explaining the image modification processing with respect to an input image of training data.

As shown in FIG. 14, in Step S31, the training data processing unit 50 acquires the training data 20 for performing learning from the training data set. In Step S32, the training data processing unit 50 receives the input image 21 included in the training data 20 and acquires the brightness adjustment parameter 2 of the input image 21 by the training model 11.

In Step S33, the training data processing unit 50 acquires the value of the loss function A related to the brightness adjustment parameter 2 using the brightness adjustment parameter 2 by the training model 11. In the first embodiment, the training data processing unit 50 acquires the output value of the loss function A according to the above Expression (1), based on the training parameter 22 (the window level $WL0$, the window width $WW_0$) included in the training data 20 and the brightness adjustment parameter 2 (the window level WL, the window width WW) as the output result of the training model 11.

In Step S34, the training data processing unit 50 optimizes the training model 11 so that the loss function A becomes smaller. The training data processing unit 50 learns the internal parameter of the training model 11 for outputting the brightness adjustment parameter 2 (the window level WL, the window width WW) that minimizes the output value of the loss function A. Machine learning for one training data 20 is performed by Steps S31 to S34.

In Step S35, the training data processing unit 50 determines whether or not there is following (untrained) training data 20 in the training data set. When there is the following training data 20, in Step S31, the following training data 20 is acquired and machine learning is performed. In Step S35, when all the learning of the training data 20 included in the training data set is completed (when there is no subsequent training data 20), the processing proceeds to Step S36.

In Step S36, the training data processing unit 50 determines whether or not the learning of the training data 20 included in the training data set has been performed a predetermined number of times set in advance. When the number of times of learning has not reached the predetermined number of times, the training data processing unit 50 repeats the processing of Steps S31 to S35 until the number of times of learning has reached the predetermined number of times. When the number of learning times has reached the predetermined number, the machine learning is completed and the trained model 10 is generated. The training data processing unit 50 stores the generated trained model 10 in the storage unit in Step S37 and terminates the processing.

In this way, the production method of the trained model 10 is carried out. The produced trained model 10 is transmitted to the image processing apparatus 100 via, e.g., a network and is stored in the storage unit 120. In a case where as shown in FIG. 12, a plurality of trained models 10 corresponding to the imaging site or the imaging purpose is produced, a data set for learning is prepared for each imaging site and imaging purpose, and Steps S31 to S37 shown in FIG. 14 are executed using the training data set for each imaging site and imaging purpose, respectively. Thus, a plurality of trained models 10 trained to output the optimal brightness adjustment parameter 2 to the radiographic image 1 corresponding to the imaging site or the imaging purpose is produced.

Note that the training data set may include a plurality of input images 21 generated by performing various image modification processing for one input image 21. For example, as shown in FIG. 15, image modification processing, such as, e.g., a rotation (A), an inversion (B), a deformation (C) such as an affine transformation, a change (D) in brightness and/or contrast, enlargement or reduction (not shown), etc., of the input image 21 are performed by randomly changing parameters. A training parameter 22 is set in each input image 21, and each is included in the training data set as separate training data 20. As a result, a large number of different input images 21 can be acquired from one input image 21, and the amount of data for converging the learning can be easily expanded.

Further, in the first embodiment, the production method of the trained model 10 may be performed by the image processing apparatus 100 in shown FIG. 13. As shown in FIG. 9, the storage unit 120 of the image processing apparatus 100 stores the training data set of the training data 20, and the processor 110 of the image processing apparatus 100 includes the training unit 114 as a functional block. The training unit 114 executes each processing of Steps S31 to S37 shown in FIG. 14.

At this time, the training unit 114 may generate new training data 20 using the radiographic image 1 acquired from the imaging unit 210 as the input image 21 and perform additional learning of the trained model 10. For example, in a case where an input (manual resetting) of the brightness adjustment parameter is performed by the operator via the operation unit 230 to the radiographic image 1 adjusted in the brightness using the brightness adjustment parameter 2 output by the parameter acquisition unit 112, the training data 20 in which the input brightness adjustment parameter is the training parameter 22 may be generated using the radiographic image 1 as the input image 21. In such a case, it is considered such that the result of the automatic brightness adjustment by the image processing apparatus 100 deviated from the optimal value, and therefore, the optimal adjustment parameter was manually set by the operator. Therefore, further optimization of the brightness adjustment processing can be achieved by performing additional learning of the trained model 10 using the training data 20 in which the manually input parameter is set as the training parameter 22.

Note that the additional learning of the trained model 10 may be performed by the training data processing unit 50 connected to the image processing apparatus 100 via a network. In this instance, the image processing apparatus 100 may transmit the training data 20 generated from the radiographic image 1 to the training data processing unit 50 and may perform additional learning of the trained model 10 in the training data processing unit 50.

Effects of First Embodiment

In this first embodiment, the following effects can be obtained.

In the production method of the trained model 10, the brightness adjustment method, and the image processing apparatus 100 according to the first embodiment, as described above, in a case where the contrast of the predetermined area PA in the brightness-adjusted image 3 becomes high with respect to the training data 20, the value in which the loss function A is relatively large is output. As a result, in the trained model 10 machine-trained by the loss function A, the predictive distribution PD of the brightness adjustment parameter 2 to be output to the radiographic image 1 can be biased in a direction of decreasing the contrast with respect to the optimal value $WW_0$. Therefore, even by the trained model 10 trained to output the optimal value $WW_0$, it is possible to suppress the output of the brightness adjustment parameter 2 so as to have a large contrast exceeding the optimal value $WW_0$. Therefore, it is possible to suppress the occurrence of halation or black defects (saturation of a pixel value) of the predetermined area PA in the brightness-adjusted image 3. As described above, in the brightness adjustment using the trained model 10 by machine learning, it is possible to suppress the occurrence of halation or black defects in the area (predetermined area PA) related to a diagnosis of a subject or the like in the image.

Note that in order to bias the predictive distribution PD of the brightness adjustment parameter 2 in the direction of decreasing the contrast with respect to the optimal value $WW_0$, for example, it is conceivable to bias the training parameter 22 in the training data 20 in a direction of decreasing the contrast with respect to the optimal value $WW_0$. In this situation, however, it is trained such that the peak of the predictive distribution PD deviates from the optimal value $WW_0$ and the brightness adjustment parameter 2 simply decreased in the contrast than the optimal value $WW_0$ is output. On the other hand, in the first embodiment, the error is biased with the training parameter 22 set as the optimal value $WW_0$. Therefore, the minimum value of the loss function A remains as the optimal value $WW_0$, and it is possible to perform the learning such that the peak of the predictive distribution PD matches the optimal value $WW_0$ as much as possible.

Further, in the first embodiment, as described above, it is configured such that in a case where halation or black defects occur due to the saturation of the pixel value in the predetermined area PA in the brightness-adjusted image 3, the loss function A outputs a relatively large value than in a case where no saturation of the pixel value occurs in the predetermined area PA. With this, in a case where halation or black defects occur in the predetermined area PA, the value of the loss function A becomes large. Therefore, it is possible to acquire the trained model 10 that has been trained in a manner biased to suppress the occurrence of halation or black defects in the predetermined area PA.

Further, in the first embodiment, as described above, in a case where the contrast of the brightness-adjusted image 3 becomes high with respect to the training data 20 than in a case where the contrast of the brightness-adjusted image 3 becomes low with respect to the training data 20, the loss function A includes a largely weighted weighting function $f(r)$. This allows the value of the loss function A to be easily biased by the weighting function.

In the first embodiment, as described above, the loss function A is a function based on the error between the training parameter 22 included in the training data 20 and the brightness adjustment parameter 2 with respect to the input image 21 included in the training data 20. With this, even by the loss function A based on the error between the training parameter 22 and the brightness adjustment parameter 2, it is possible to suppress that the error is evaluated symmetrically with respect to the optimal value $WW_0$ and relatively increase the value of the loss function A in a case where the contrast becomes high with respect to the optimal value $WW_0$. Therefore, it is possible to effectively suppress the occurrence of the saturation of the pixel value in the predetermined area PA.

Further, in the first embodiment, as described above, the predetermined area PA includes at least a part of the area reflecting the subject. With this, by using the brightness adjustment parameter 2 output by the trained model 10, it is possible to assuredly suppress the occurrence of halation or black defects in the area reflecting the subject.

Further, in the first embodiment, as described above, the brightness adjustment parameter 2 includes the window level WL that defines the median of the pixel value range to be converted to the brightness-adjusted image 3 in the radiographic image 1 and the window width WW that defines the size of the pixel value range. As a result, the magnitude of the contrast of the pixel value in the predetermined area PA can be adjusted by the value of the window width WW. Therefore, it is possible to easily evaluate the contrast by the loss function A, as compared with the case where a large number of parameters affect the contrast.

Further, in the first embodiment, as described above, it is further provided with a step of acquiring the information 5 related to the imaging site or the imaging purpose of the subject. In the step of acquiring the brightness adjustment parameter 2, based on the information 5 related to the imaging site or the imaging purpose, the learned model 10 for adjusting the brightness among from the plurality of the trained model 10 is selected. As described above, by preparing a plurality of trained models 10 separately trained according to the imaging site or the imaging purpose and selecting the trained model 10 based on the information 5 related to the imaging site or the imaging purpose, the optimum brightness adjustment according to the imaging site or the imaging purpose can be performed.

Second Embodiment

Next, referring to FIG. 16 to FIG. 18, the production method of the trained model and the brightness adjustment method according to a second embodiment will be described. In the second embodiment, a loss function A will be described with reference to an example about a function based on the comparison between the training data 20 and the brightness-adjusted image 3 unlike a function based on the error between the training parameter 22 and the brightness adjustment parameter 2 in the above-described first embodiment. In the second embodiment, the same components as those of the first embodiment are denoted by the same reference numerals, and the description thereof are omitted.

Figure 16:
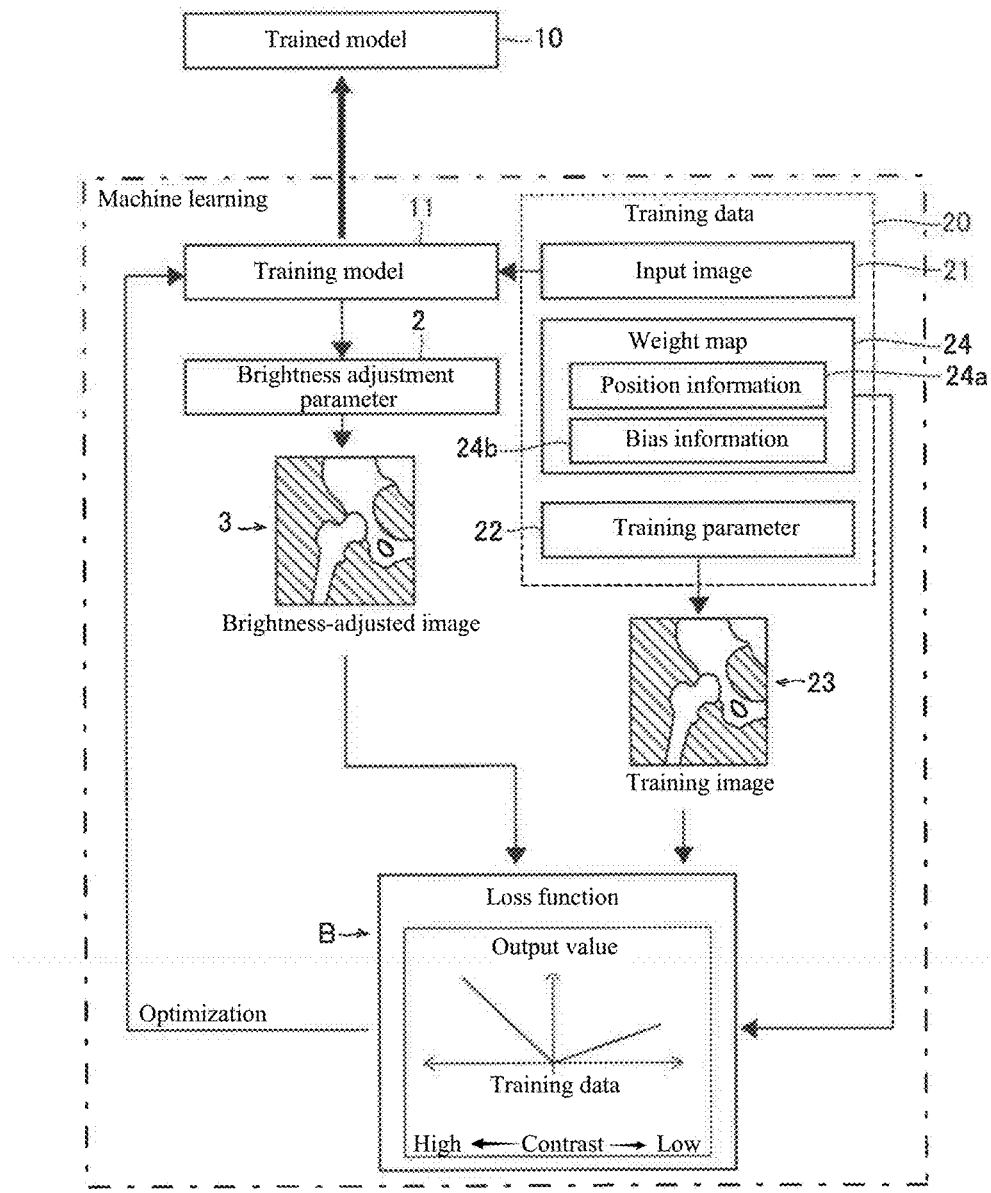
FIG. 16 is a diagram showing a loss function and training data according to a second embodiment.

As shown in FIG. 16, in the second embodiment, the trained model 10 is generated by learning of performing the optimization of the loss function B related to the brightness adjustment parameter 2. The loss function B is a function based on the comparison between the pixel value of the training image 23 included in the training data 20 and the pixel value of the brightness-adjusted image 3 in which the input image 21 included in the training data 20 is adjusted in the brightness based on the brightness adjustment parameter 2.

Specifically, in the second embodiment, in the machine learning, the brightness-adjusted image 3 is acquired based on the brightness adjustment parameter 2 output by the training model 11 which is being trained by inputting the input image 21 included in the training data 20. The training image 23 adjusted in the brightness is acquired based on the input image 21 included in the training data 20 and the training parameter 22. The brightness-adjusted image 3 and the training image 23 are images respectively acquired by adjusting the brightness with respect to the same input image 21 included in the training data 20. The training image 23 is a ground truth image of the machine learning adjusted in the brightness based on the optimal value of the brightness adjustment parameter.

Then, the loss function B is configured as a function based on the comparison between the pixel value of the training image 23 and the pixel value of the brightness-adjusted image 3 in the same pixel of both images. With this, in the second embodiment, based on the resulting image actually adjusted in the brightness by the brightness adjustment parameter 2, the difference between the output result of the training model 11 and the training data 20 is evaluated.

For example, the loss function B is a function based on the difference of the pixel value of the corresponding pixel between the brightness-adjusted image 3 and the training image 23. Specifically, as shown in the following Expression (3), the loss function B is a mean square error acquired by integrating the weight to the difference in the pixel value of the corresponding pixel between the brightness-adjusted image 3 and the training image 23.

$$B = \sqrt{\sum_y \sum_x \{k(x,y) f(I(x,y) - I_0(x,y))\}^2} \quad (3)$$

However, $$\begin{cases} \text{when } I(x,y) = 0 \text{ or } I_{max}, & f(r) = wr, \\ \text{when } I(x,y) = 0 \text{ or other than } I_{max}, & f(r) = r, \end{cases}$$

where x and y are coordinates of the respective images (the brightness-adjusted image 3, the training image 23), respectively. k (x, y) is the weight at each coordinate (x, y). I (x,y) is a pixel value at the coordinate (x, y) of the brightness-adjusted image 3, and Jo (x, y) is a pixel value at the coordinate (x, y) of the training image 23. f(r) is a weighting function. w is the value of the weight (w>1). $I_{max}$ is the maximum value a pixel value (=255).

Similar to the first embodiment, in a case where the contrast of the brightness-adjusted image 3 becomes high with respect to the training data 20 (I (x, y)=0, or $I_{max}$) than in a case where the contrast of the brightness-adjusted image 3 becomes high with respect to the training data 20 (I (x, y)=0, or other than $I_{max}$), the loss function B includes a heavily weighted weighting function In other words, in a case where the window width WW becomes smaller than the optimal value $WW_0$ (when the contrast becomes high), a pixel in which the pixel value I is saturated occurs in the predetermined area PA. In other words, in the pixel in which the optimal pixel value $I_0$ becomes $0 < I_0 < I_{max}$, the pixel value I (x, y) becomes the lowest value 0 (black defects) or the highest value $I_{max}$ (halation). In this case, the loss function B estimates the error relatively large by integrating the weight w to the error $(I - I_0)$. As a result, in a case where the contrast of the predetermined area PA of the brightness-adjusted image 3 becomes high with respect to the training data 20 (when I (x, y)=0 or $I_{max}$), the loss function B of the second embodiment outputs a relatively large value to bias the learning in a direction of decreasing the contrast. In a case where the window width WW becomes larger than the optimal value $WW_0$ (when the contrast becomes low), it is considered that no pixel in which the pixel value I is saturated in the predetermined area PA occurs. Therefore, the loss function B estimates the error relatively small without the accumulation of the weight w.

Furthermore, in the second embodiment, the loss function B may include a weight k (x, y) set for each pixel (position coordinate) in the image. Therefore, in the second embodiment, different weights k can be set for each area in the image. For example, in the second embodiment, as shown in FIG. 17, in a case where saturation of the pixel value in the predetermined area PA in the image occurs by the weight k, the loss function B is configured to output a value larger than in a case where the saturation of the pixel value occurs in the area PB other than the predetermined area PA. Thus, in a case where the contrast of the brightness-adjusted image 3 becomes high with respect to the training data 20 (training mage 23) (when saturation of the pixel value occurs) in the predetermined area PA, the value of the loss function B is estimated relatively large, and the learning is performed strongly in the direction of suppressing the occurrence of the saturation of the pixel value by suppressing the contrast. On the other hand, in the area PB other than the predetermined area PA, in a case where the contrast of the brightness-adjusted image 3 becomes high with respect to the training data 20 (training image 23), the value of the loss function B is estimated relatively small, and it is trained so as not to suppress the contrast unnecessarily.

As described above, in order to set the weight k for each pixel in the image (position coordinate), in the training data 20 of the second embodiment, as shown in FIG. 16, the position information 24a in the predetermined area PA and the bias information 24b of the loss function B are included. The position information 24a is the information of the position coordinate in the image. The bias information 24b is a set value of the weight k.

Specifically, the training data 20 includes a weight map 24 including the position information 24a in the input image 21 and the bias information 24b. The weight map 24 includes, as the position information 24a, the area to which the common weight k is applied in the input image 21. The weight map 24 includes, as the bias information 24b, the values of the weight k applied to the area partitioned as the position information 24a in the input image 21.

Figure 17:
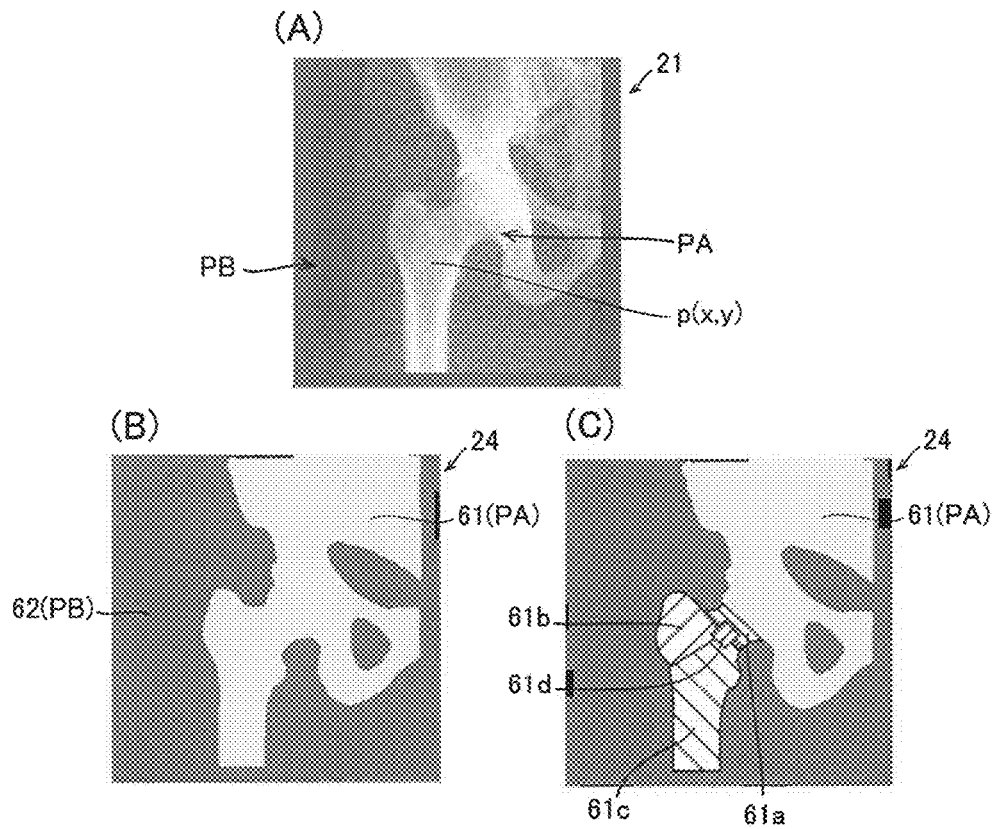
FIG. 17 shows an input image (A) and examples (B) and (C) of a weight map with respect to the input image.

For example, as shown in (B) of FIG. 17, the position information 24a can be set so as to partition the input image 21 into the area 61 reflecting the subject SB and the background area 62. In this case, the bias information 24b includes the weight k different for the area 61 reflecting the subject SB and the background area 62, in response to the position information 24a. In the example of (B) of FIG. 17, the area reflecting the subject SB is the predetermined area PA. The weight k of the area 61 reflecting the subject SB is set to be higher than the weight of the background area 62. The area 61 may be set to a weight k=10, and the background area 62 may be set to a non-weight (k=1).

The position information 24a may be set to further segment the interior of the area 61 reflecting the subject SB, for example, as shown in (C) of FIG. 17. That is, among the area 61 reflecting the subject SB, it is possible to distinguish the area having a high diagnosis importance from the area having a relatively low diagnosis importance. In addition, the ease of saturation of a pixel value may differ for each site of the subject depending on the morphological condition, such as, e.g., the anatomy of the subject. In this instance, the position information 24a may be set by dividing the inside of the area 61 reflecting the subject SB into a plurality of partial areas, and the bias information 24b (weight k) may be set for each partial area. In the example shown in (C) of FIG. 17, an example is shown in which the same or different weights k are respectively set to the respective partial areas of the femoral neck 61a, the greater trochanter 61b, the diaphyseal portion 61c, and the ward triangle 61d in accordance with the anatomy of the lumbar portion of the subject.

By the weight map 24, for the pixel p (x, y) at any position coordinate of the input image 21, the weight k (x, y) set in the area to which the pixel p belongs is acquired. As a result, in the loss function B, the magnitude of the bias is set for each position in the input image 21, based on the position information 24a in the predetermined area PA included in the training data 20 and the bias information 24b of the loss function B.

Consequently, in a case where saturation of a pixel value occurs in the predetermined area PA in the image, the loss function B is configured to output a value larger than in a case where saturation of a pixel value occurs in an area other than the predetermined area PA.

The effect of the learning bias by the loss function B in the second embodiment on the brightness adjustment parameter 2 output by the trained model 10 is described.

Figure 18:
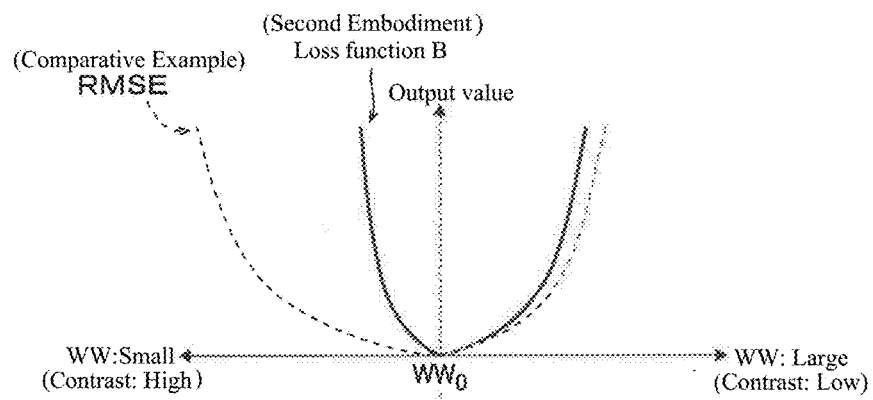
FIG. 18 is a diagram showing the change (A) in the loss coefficient and the predictive distribution (B) of the brightness adjustment parameter according to the second embodiment.
Figure 18:
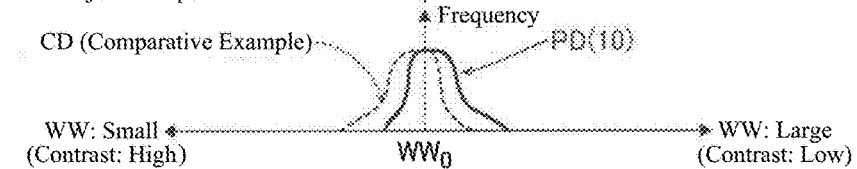

FIG. 18 is a graph showing the changes in the output value of the loss function B and the predictive distribution PD of the window width WW output by the trained model 10 optimized using the loss function B, with respect to the window width WW.

As Comparative Example, a case in which without performing weighting, a loss function RMSE by the mean square error of the pixel value of the corresponding pixel of the brightness-adjusted image 3 and the training image 23 is shown with dashed lines. The loss function RMSE of Comparative Example is represented by the following Expression (4).

$$RMSE = \sqrt{\Sigma_y \Sigma_x (I(x,y) - I_0(x,y))^2} \quad (4)$$

In the above Expression (4), in the loss function RMSE according to Comparative Example, when halation or black defects (saturation of a pixel value) occur in the brightness-adjusted image, it is underestimated by the amount that the pixel value of the area is saturated. That is, as shown in (A) of FIG. 18, the output value of the loss function in a case where the window width WW is smaller than the optimal value $WW_0$ and saturation of the pixel values is occurring becomes relatively smaller than the output value of the loss function in a case where the window width WW is larger than the optimal value $WW_0$ and no saturation of the pixel value is occurring. Therefore, as shown in (B) of FIG. 18, it is considered that the predictive distribution CD of the output result of the trained model output optimized by using the loss function RMSE becomes asymmetrically distributed in the direction in which halation or black defects (saturation of pixel value) occur with respect to the optimal value $WW_0$ (in a direction of decreasing the window width WW). In the trained model optimized using the loss function RMSE according to Comparative Example, there is a possibility that saturation of a pixel value occurs in the predetermined area PA in more than half of the window width WW to be output.

On the other hand, in the loss function B shown by the solid line in FIG. 18, when halation or black defects (saturation of a pixel value) occur in the brightness-adjusted image (I=0 or $I_{max}$), the weight w is estimated relatively large by integrating the weight W to the error of the pixel value in the area. In a case where no halation or black defects (saturation of pixel value) is occurring ($0<I<I_{max}$), the weight w is not accumulated, and the error of the pixel value of the area is estimated to be relatively small. Note that for the pixel for which both the optimal pixel value $I_0$ and the pixel value I are 0 or $I_{max}$, the weight w is integrated in the calculation, but since the error becomes 0, it does not affect the loss function B. Therefore, the predictive distribution PD of the output result of the trained model 10 optimized using the loss function B of the first embodiment becomes a distribution biased such that the predictive distribution PD is smaller in the direction in which the pixel value is likely to saturate and the contrast becomes high (the direction in which the window width WW becomes smaller) and larger in the direction in which the contrast becomes low (the direction in which the window width WW becomes larger) with respect to the optimal value $WW_0$.

As a result, as can be seen from the predictive distribution PD, in the trained model 10 optimized using the loss function B of the first embodiment, it is suppressed that the window width WW to be output varies in the direction of increasing the contrast exceeding the optimal value $WW_0$ (in the direction of decreasing the window width WW to be output). Thus, the possibility of occurrence of saturation of the pixel value in the predetermined area PA is suppressed.

The rest of the configuration of the second embodiment is the same as that of the first embodiment. In the second embodiment, the production method of the trained model 10, the brightness adjustment method, and the image processing apparatus 100 are the same except that the loss function B differs from the first embodiment, and therefore the descriptions thereof are omitted.

Effects of Second Embodiment

In this second embodiment, the following effects can be acquired.

In the second embodiment, in the same manner as in the first embodiment, it is possible to suppress the occurrence of halation or black defects in the area (predetermined area PA) related to a diagnose of a subject or the like in the image in the brightness adjustment using the trained model 10 by machine learning.

Further, in the second embodiment, as described above, the loss function B is a function based on the comparison between the pixel value of the training image 23 included in the training data 20 and the pixel value of the brightness-adjusted image 3 in which the input image 21 included in the training data 20 is adjusted in the brightness based on the brightness adjustment parameter 2. With this, even by the loss function B based on the comparison of the pixel value between the training image 23 and the brightness-adjusted image 3, it is possible to relatively increase the value of the loss function B in a case where the contrast becomes high with respect to the optimal value and suppress the underestimation of the error due to the saturation of the pixel. Therefore, it is possible to effectively suppress the occurrence of the saturation of the pixel value in the predetermined area PA.

Further, in the second embodiment, as described above, the loss function B is configured such that, when saturation of the pixel value occurs in the predetermined area PA in the image, a value larger in the case where saturation of the pixel value occurs in an area other than the predetermined area PA is output. With this, it is possible to suppress the learning from being affected by the error in the area PB with less importance other than the predetermined area PA while suppressing the occurrence of saturation of a pixel value saturation in the predetermined area PA.

In the second embodiment, as described above, in the loss function B, the magnitude of the bias is set for each position in the input image 21, based on the position information 24a in the predetermined area PA included in the training data 20 and the bias information 24b of the loss function B. This makes it possible to distinguish between the predetermined area PA and the area PB other than the predetermined area PA based on the position information 24a in the predetermined area PA and specify the magnitude relation of the bias of the loss function B between the predetermined area PA and the area PB other than the predetermined area PA based on the bias information 24b of the loss function B. Therefore, the magnitude (weight k) of the bias of the loss function B can be easily changed according to the area in the image.

The other effects of the second embodiment are the same as those of the first embodiment.

(Modifications)

It should be understood that the embodiments disclosed here are examples in all respects and are not restrictive. The scope of the present invention is shown in the claims rather than by the above-described embodiments, and the scope of the present invention includes all modifications (modified examples) within the meanings and ranges equivalent to the claims.

For example, in the above-described first and second embodiments, as the example of the loss function, the loss function A and the loss function B according to the mean square error are shown, but the present invention is not limited thereto. In the present invention, the loss function may be configured by a function other than the mean square error. For example, as the loss function B of the second embodiment, a function, such as, e.g., a PSNR (Peak signal-to-noise ratio) or an SSIM (Structural SIMilarity) may be used. However, for example, the SSIM can evaluate the similarity between images, but it is an index that also evaluates the structural element unrelated to the brightness adjustment, such as, e.g., the misalignment of images. Therefore, the mean square error that simply evaluates only the pixel value (brightness) between images is more suitable as the loss function for use in the training model for the brightness adjustment.

Further, in the first and second embodiments described above, an example is shown in which a large weight w ($>1$) is applied when the contrast in the predetermined area PA becomes high with respect to the training data 20, but the present invention is not limited thereto. It may be configured such that a smaller weight w ($<1$) is applied when the contrast in the predetermined area PA becomes low with respect to the training data 20 so that the output value when the contrast in the predetermined area PA becomes larger is set to be relatively larger.

Further, in the first and second embodiments, an example is shown in which the predetermined area PA includes at least a part of the area reflecting a subject, but the present invention is not limited thereto. The predetermined area PA may be set according to the application of the radiographic image 1 and may be an area other than an area reflecting a subject.

Further, in the first and second embodiments, an example is shown in which the output value of the loss function is biased by including the weighting function in the loss function, but the present invention is not limited thereto. For example, the output of the loss function may be biased by applying different loss functions when the contrast in the predetermined area PA becomes high with respect to the training data 20 and when the contrast of the predetermined area PA becomes low with respect to the training data 20.

Further, in the second embodiment described above, an example is shown in which the weight k is differentiated between the predetermined area PA and an area PA other than the predetermined area PA using the weight map 24, but the present invention is not limited thereto. In the present invention, the weight k may not be set differentiated for each area. In the loss function B, the weight k may not be included. In this case, the training data 20 is not required to include the weight map 24.

Further, in the second embodiment, an example is shown in which the training image 23 is acquired based on the training parameter 22 included in the training data 20, but the present invention is not limited thereto. In the present invention, the training data 20 may necessarily include the training image 23. In this instance, the training data 20 may not necessarily be required to include the training parameter 22.

Further, in the first and second embodiments, an example is shown in which the trained model 10 to be used for the brightness adjustment is selected from a plurality of trained models 10 by acquiring the information 5 related to the imaging site or the imaging purpose, but the present invention is not limited thereto. In the present invention, the information 5 about the imaging site or the imaging purpose is not always required to be acquired. That is, it is not necessary to select the trained model 10.

Note that the acquisition of the information 5 about the imaging site or the imaging purpose is not limited to the method using the operation unit 230, and the information 5 about the imaging site or the imaging purpose may be acquired by recognizing, e.g., the image of the input radiographic image 1.

Further, in the first and second embodiments, an example is shown in which the brightness adjustment parameter 2 includes the window level WL and the window width WW, but the present invention is not limited thereto. For example, instead of the window width WW, the brightness adjustment parameter 2 may include the upper limit VH and the lower limit VL of the window width.

DESCRIPTION OF SYMBOLS

1: Radiographic image
2: Brightness adjustment parameter
3: Brightness-adjusted image
5: Information related to imaging site or imaging purpose
10: Trained model
11: Training model
20: Training data
21: Input image
22: Training parameter
23: Training image
24a: Position information
24b: Bias information
100: Image processing apparatus
111: Image acquisition unit
112: Parameter acquisition unit
113: Adjustment processing unit
120: Storage unit
A, B: Loss function
PA: Predetermined area
PB: Area other than predetermined area
WL: Window level
WW: Window width
f(r): Weighting function

The invention claimed is:

1. A method of producing a trained model by machine learning using training data including an input training image and ground truth data, the trained model configured for receiving an input radiographic image reflecting a subject to output a brightness adjustment parameter of the radiographic image, the method comprising:

inputting the training image to a training model, the training model being under production, to output a brightness adjustment parameter;

acquiring a value of a loss function based on the output brightness adjustment parameter and the ground truth; and adjusting the value of the loss function to be decreased, to optimize the training model, wherein the adjusting the value of the loss function includes adjusting the loss function so that the value thereof is higher in a first situation compared to a second situation, causing a brightness-adjusted image, generated based upon the output brightness adjustment parameter, to have a higher contrast in a predetermined area therein, wherein the first situation being such that the contrast of a predetermined area becomes higher compared to the training image, and wherein the second situation being such that the contrast of a predetermined area becomes lower compared to the training image.

2. The method of producing a trained model as recited in claim 1, wherein in a case where halation or black defects occur due to saturation of a pixel value in the predetermined area in the brightness-adjusted image, the loss function is configured to output a larger value than in a case where saturation of a pixel value does not occur in the predetermined area.

3. The method of producing a trained model as recited in claim 1, wherein a weighted weighting function of the loss function in a case of the first situation is larger than the weighted weighting function of the loss function in a case of the second situation.

4. The method of producing a trained model as recited in claim 1, wherein the loss function is a function based on an error between a training parameter included in the training data and the brightness adjustment parameter with respect to the input image included in the training data.

5. The method of producing a trained model as recited in claim 1, wherein the loss function is a function based on a comparison between a pixel value of a training image included in the training data and a pixel value of the brightness-adjusted image in which the input image included in the training data has been adjusted in brightness based on the brightness adjustment parameter.

6. The method of producing a trained model as recited in claim 5, wherein in a case where saturation of a pixel value occurs in the predetermined area in the image, the loss function is configured to output a value larger than in a case where saturation of a pixel value occurs in an area other than the predetermined area.

7. The method of producing a trained model as recited in claim 6, wherein the loss function is set in magnitude of bias for each position in the input image, based on position information of the predetermined area included in the training data and bias information of the loss function.

8. The method of producing a trained model as recited in claim 1,
wherein the predetermined area includes at least a part of an area reflecting the subject.

9. The method of producing a trained model as recited in claim 1,
wherein the brightness adjustment parameter includes a window level that defines a median of a pixel value range to be converted to the brightness-adjusted image in the radiographic image and a window width that defines magnitude of the pixel value range.

10. A brightness adjustment method using machine learning, which uses training data including an input training image and ground truth data, the trained model configured for receiving an input radiographic image reflecting a subject to output a brightness adjustment parameter of the radiographic image, the brightness adjustment method comprising:
acquiring the radiographic image;
acquiring the brightness adjustment parameter with respect to the radiographic image using a trained model by the machine learning; and
acquiring a brightness-adjusted image by adjusting brightness of the radiographic image based on the brightness adjustment parameter,
wherein the trained model is generated by learning that optimizes a loss function—to optimize the training model,
the loss function is adjusted so that a value thereof is higher in a first situation compared to a second situation, causing a brightness-adjusted image, generated based upon the output brightness adjustment parameter, to have a higher contrast in a predetermined area therein,
wherein the first situation being such that the contrast of a predetermined area becomes higher compared to the training image, and
wherein the second situation being such that the contrast of a predetermined area becomes lower compared to the training image.

11. The brightness adjustment method as recited in claim 10, further comprising:
a step of acquiring information related to an imaging site or an imaging purpose of the subject,
wherein in the step of acquiring the brightness adjustment parameter, the trained model for use in the brightness adjustment from a plurality of the trained models is selected based on the information related to the imaging site or the imaging purpose.

12. An image processing apparatus comprising:
an image acquisition unit configured to acquire a radiographic image;
a storage unit configured to store a trained model by machine learning in which a radiographic image reflecting a subject is input and a brightness adjustment parameter of the radiographic image is output;
a parameter acquisition unit configured to acquire the brightness adjustment parameter with respect to the radiographic image using the trained model; and
an adjustment processing unit configured to acquire a brightness-adjusted image by adjusting brightness of the radiographic image based on the brightness adjustment parameter,
wherein the trained model is generated by learning that optimizes a loss function to be decreased, to optimize the training model,
wherein the loss function is adjusted so that a value thereof is higher in a first situation compared to a second situation, causing a brightness-adjusted image, generated based upon the brightness adjustment parameter, to have a higher contrast in a predetermined area therein,
wherein the first situation being such that the contrast of a predetermined area becomes higher compared to the training image, and
wherein the second situation being such that the contrast of a predetermined area becomes lower compared to the training image.

* * * * *